US012383349B2

(12) United States Patent
Naumann et al.

(10) Patent No.: US 12,383,349 B2
(45) Date of Patent: Aug. 12, 2025

(54) SYSTEMS AND METHODS FOR WIRELESS LOCALIZATION

(71) Applicant: Elucent Medical, Inc., Eden Prairie, MN (US)

(72) Inventors: Charles Foard Naumann, Eden Prairie, MN (US); Bryan Dean, Eden Prairie, MN (US); Jeff Kotula, Eden Prairie, MN (US); Jason Hiltner, Eden Prairie, MN (US)

(73) Assignee: Elucent Medical, Inc., Eden Prairie, MN (US)

( * ) Notice: Subject to any disclaimer, the term of this patent is extended or adjusted under 35 U.S.C. 154(b) by 0 days.

(21) Appl. No.: 18/359,417

(22) Filed: Jul. 26, 2023

(65) Prior Publication Data

US 2024/0033010 A1 Feb. 1, 2024

Related U.S. Application Data

(60) Provisional application No. 63/424,977, filed on Nov. 14, 2022, provisional application No. 63/392,177, filed on Jul. 26, 2022.

(51) Int. Cl.
*A61B 34/20* (2016.01)
*A61B 90/00* (2016.01)

(52) U.S. Cl.
CPC ............ *A61B 34/20* (2016.02); *A61B 90/361* (2016.02); *A61B 2034/2051* (2016.02)

(58) Field of Classification Search
CPC .................. A61B 34/20; A61B 90/361; A61B 2034/2051; A61B 2017/07271;
(Continued)

(56) References Cited

U.S. PATENT DOCUMENTS 5,211,129 A   5/1993   Taylor et al.
6,026,818 A   2/2000   Blair et al.
(Continued)

FOREIGN PATENT DOCUMENTS

WO   WO 2018/049518 A1   3/2018
WO   WO 2020/254875 A1   12/2020
(Continued)

OTHER PUBLICATIONS

International Search Report & Written Opinion, Application No. PCT/US2023/071021, dated Feb. 23, 2024, 16 pages.

*Primary Examiner* — Pascal M Bui Pho
*Assistant Examiner* — Michael Yiming Fang
(74) *Attorney, Agent, or Firm* — CASIMIR JONES, S.C.; Brian F. Bradley

(57) ABSTRACT

A wireless localization system including an exciter coil, a sensor coil, a surgical tool including a head defining a longitudinal axis, and a first wireless tag coupled to the head at a first position along the longitudinal axis. The first wireless tag is configured to generate a first signal in response to a magnetic field generated by the exciter coil. The wireless localization system further includes a second wireless tag coupled to the head at a second position along the longitudinal axis, the second position is spaced from the first position. The second wireless tag is configured to generate a second signal in response to the magnetic field generated by the excited coil. The wireless localization system further includes a processor that determines the location of the head based on the first signal and the second signal detected by the sensor coil.

20 Claims, 27 Drawing Sheets

(58) Field of Classification Search
CPC . A61B 34/25; A61B 90/98; A61B 2017/0053;
A61B 2017/00973; A61B 2090/3983;
A61B 17/07207; A61B 90/39; A61B
2090/3937; A61B 17/068; A61B 17/072;
A61B 17/083; A61B 17/00; A61B
2017/00
See application file for complete search history.

(56) References Cited

U.S. PATENT DOCUMENTS

| | | | |
|---|---|---|---|
| 6,216,029 B1 * | 4/2001 | Paltieli | A61B 34/20 600/461 |
| 6,363,940 B1 | 4/2002 | Krag | |
| 6,675,810 B2 | 1/2004 | Krag | |
| 6,698,433 B2 | 3/2004 | Krag | |
| 6,812,842 B2 | 11/2004 | Dimmer | |
| 6,822,570 B2 | 11/2004 | Dimmer et al. | |
| 6,838,990 B2 | 1/2005 | Dimmer | |
| 6,889,833 B2 | 5/2005 | Seiler et al. | |
| 6,977,504 B2 | 12/2005 | Wright et al. | |
| 7,026,927 B2 | 4/2006 | Wright et al. | |
| 7,135,978 B2 | 11/2006 | Gisselberg et al. | |
| 7,174,201 B2 | 2/2007 | Govari et al. | |
| 7,176,798 B2 | 2/2007 | Dimmer et al. | |
| 7,289,839 B2 | 10/2007 | Dimmer et al. | |
| 7,407,054 B2 | 8/2008 | Seiler et al. | |
| 7,414,404 B2 | 8/2008 | Keene | |
| 7,575,550 B1 | 8/2009 | Govari | |
| 7,590,441 B2 | 9/2009 | Govari et al. | |
| 7,657,301 B2 | 2/2010 | Mate et al. | |
| 7,657,302 B2 | 2/2010 | Mate et al. | |
| 7,657,303 B2 | 2/2010 | Mate et al. | |
| 7,684,849 B2 | 3/2010 | Wright et al. | |
| 7,696,876 B2 | 4/2010 | Dimmer et al. | |
| 7,728,868 B2 | 6/2010 | Razzaque et al. | |
| 7,747,307 B2 | 6/2010 | Wright et al. | |
| 7,778,687 B2 | 8/2010 | Dimmer et al. | |
| 7,899,513 B2 | 3/2011 | Phillips et al. | |
| 7,912,529 B2 | 3/2011 | Herron et al. | |
| 7,926,491 B2 | 4/2011 | Wright et al. | |
| 8,011,508 B2 | 9/2011 | Seiler et al. | |
| 8,113,210 B2 | 2/2012 | Petcavich et al. | |
| 8,196,589 B2 | 6/2012 | Gisselberg et al. | |
| 8,340,379 B2 | 12/2012 | Razzaque et al. | |
| 8,350,902 B2 | 1/2013 | Razzaque et al. | |
| 8,452,375 B2 | 5/2013 | Krag et al. | |
| 8,482,606 B2 | 7/2013 | Razzaque et al. | |
| 8,554,307 B2 | 10/2013 | Razzaque et al. | |
| 8,585,598 B2 | 11/2013 | Razzaque et al. | |
| 8,641,621 B2 | 2/2014 | Razzaque et al. | |
| 8,670,816 B2 | 3/2014 | Green et al. | |
| 8,690,776 B2 | 4/2014 | Razzaque et al. | |
| 8,831,310 B2 | 9/2014 | Razzaque et al. | |
| 8,857,043 B2 | 10/2014 | Dimmer et al. | |
| 8,892,185 B2 | 11/2014 | Chi Sing et al. | |
| 8,926,511 B2 | 1/2015 | Bar-Tal | |
| 8,939,153 B1 | 1/2015 | Reicher et al. | |
| 8,968,171 B2 | 3/2015 | Mckenna et al. | |
| 8,973,584 B2 | 3/2015 | Brander et al. | |
| 9,084,888 B2 | 7/2015 | Poulsen et al. | |
| 9,107,698 B2 | 8/2015 | Razzaque et al. | |
| 9,282,947 B2 | 3/2016 | Razzaque et al. | |
| 9,283,053 B2 | 3/2016 | Mayse et al. | |
| 9,364,294 B2 | 6/2016 | Razzaque et al. | |
| 9,386,942 B2 | 7/2016 | Chi Sing et al. | |
| 9,398,936 B2 | 7/2016 | Razzaque et al. | |
| 9,545,506 B2 | 1/2017 | Quigley | |
| 9,659,345 B2 | 5/2017 | Razzaque et al. | |
| 9,675,319 B1 | 6/2017 | Razzaque et al. | |
| 9,901,406 B2 | 2/2018 | State et al. | |
| 10,195,464 B2 | 2/2019 | Vertatschitsch et al. | |
| 10,293,135 B2 | 5/2019 | Quigley | |
| 10,499,832 B2 | 12/2019 | Greene et al. | |
| 10,524,693 B2 | 1/2020 | Freysinger et al. | |
| 10,610,326 B2 | 4/2020 | Rulkov et al. | |
| 10,653,496 B2 | 5/2020 | Mayse et al. | |
| 10,827,949 B2 | 11/2020 | Greene et al. | |
| 10,835,150 B2 | 11/2020 | Chi Sing et al. | |
| 11,179,220 B2 | 11/2021 | Chi Sing et al. | |
| 11,191,445 B2 | 12/2021 | Greene et al. | |
| 11,234,732 B2 | 2/2022 | Bueno et al. | |
| 11,291,384 B2 | 4/2022 | Ravi et al. | |
| 11,351,008 B2 | 6/2022 | Rulkov et al. | |
| 11,439,847 B2 | 9/2022 | Vertatschitsch et al. | |
| 11,484,219 B2 | 11/2022 | Greene et al. | |
| 2003/0018246 A1 | 1/2003 | Govari et al. | |
| 2007/0265491 A1 * | 11/2007 | Krag | A61B 17/32053 600/37 |
| 2008/0218311 A1 * | 9/2008 | Pless | G07C 9/28 340/5.81 |
| 2009/0118742 A1 * | 5/2009 | Hartmann | A61B 34/20 901/14 |
| 2009/0216115 A1 | 8/2009 | Seiler et al. | |
| 2010/0072994 A1 * | 3/2010 | Lee | A61B 5/14503 324/307 |
| 2010/0298705 A1 * | 11/2010 | Pelissier | A61B 8/4254 600/443 |
| 2013/0018259 A1 | 1/2013 | Borillo et al. | |
| 2016/0213431 A1 | 7/2016 | Bueno et al. | |
| 2017/0095315 A1 * | 4/2017 | Rudie | A61B 18/1402 |
| 2018/0042517 A1 * | 2/2018 | van der Weide | A61B 34/20 |
| 2018/0289444 A1 | 10/2018 | Blair et al. | |
| 2020/0107885 A1 * | 4/2020 | Palushi | A61B 34/20 |
| 2020/0298021 A1 | 9/2020 | Ravi et al. | |
| 2020/0405302 A1 * | 12/2020 | Shelton, IV | A61B 17/07207 |
| 2021/0153970 A1 * | 5/2021 | Agostinelli | A61B 90/39 |
| 2021/0204832 A1 | 7/2021 | Chin Sing et al. | |
| 2022/0047338 A1 * | 2/2022 | Mucha | A61B 5/062 |
| 2022/0054203 A1 | 2/2022 | Rudie et al. | |
| 2022/0151726 A1 | 5/2022 | Chi Sing et al. | |
| 2022/0209586 A1 | 6/2022 | Kyaw et al. | |
| 2022/0273340 A1 | 9/2022 | Bueno et al. | |
| 2023/0023448 A1 | 1/2023 | Ravi et al. | |
| 2023/0172635 A1 | 6/2023 | Bueno et al. | |
| 2023/0172636 A1 | 6/2023 | Bueno et al. | |
| 2023/0252257 A1 * | 8/2023 | Hoegerle | A61B 90/98 340/572.8 |
| 2023/0355234 A1 * | 11/2023 | Heerink | A61B 17/072 |
| 2024/0027176 A1 * | 1/2024 | Biancalana | G01R 33/0206 |
| 2024/0041488 A1 * | 2/2024 | Shelton, IV | A61B 17/2841 |
| 2024/0057889 A1 * | 2/2024 | Ramirez | A61B 5/061 |

FOREIGN PATENT DOCUMENTS

| | | |
|---|---|---|
| WO | 2021-097197 | 5/2021 |
| WO | WO 2023/205496 | 10/2023 |

* cited by examiner

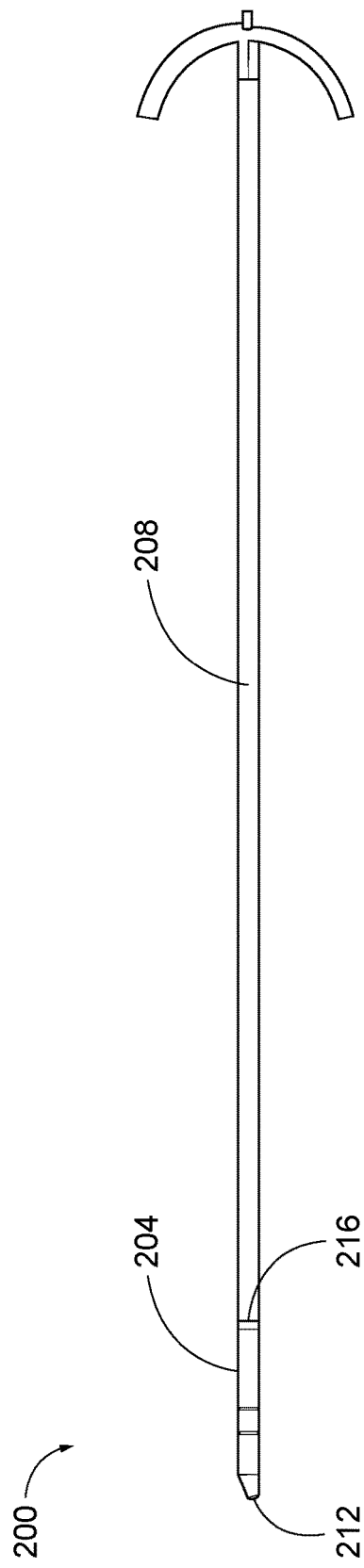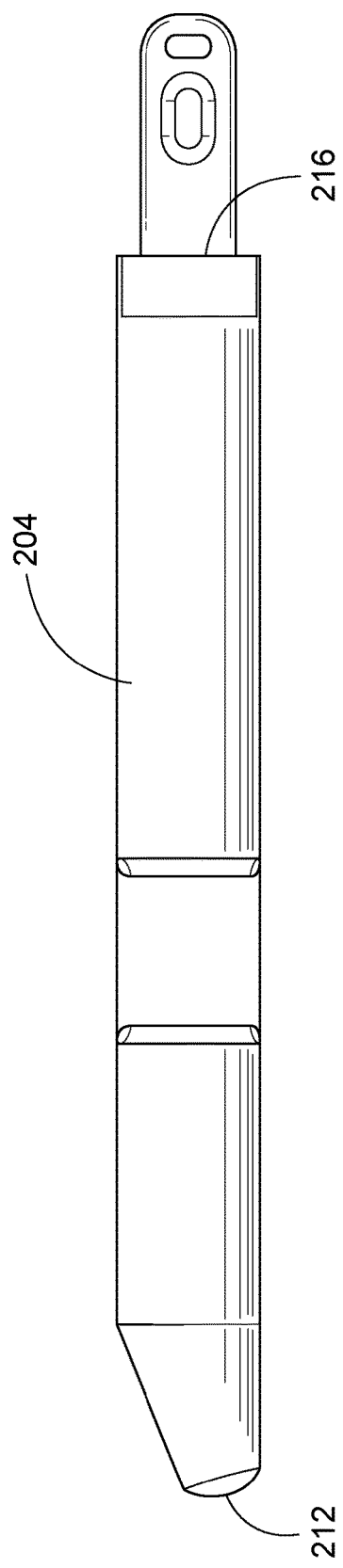
FIG. 8
FIG. 9

SYSTEMS AND METHODS FOR WIRELESS LOCALIZATION

CROSS-REFERENCE TO RELATED APPLICATIONS

This application claims priority to and the benefit of U.S. Provisional Patent Application No. 63/392,177, filed Jul. 26, 2022, and U.S. Provisional Patent Application No. 63/424,977, filed Nov. 14, 2022, and are incorporated herein by reference in their entirety for all purposes.

TECHNICAL FIELD

The present disclosure relates systems, devices, assemblies, and methods for wireless localization in surgical and medical procedures. The systems, devices, assemblies, and methods find use in a variety of applications including integration with a surgical tool.

BACKGROUND

A common and serious challenge for many medical procedures is the accurate location of treatment areas. For example, the location of lesions, such as tumors that are to undergo treatment, including surgical resection, continues to present a challenge to the medical community. Existing systems are expensive, complex, time-consuming, and often unpleasant for the patient.

Such issues are illustrated by the conventional surgical treatment of pulmonary nodules. In some cases where pulmonary nodules may be difficult to locate at conventional open surgery or at thoracoscopy, a hook wire, injection or visible dye, or a radionuclide is placed in or around the nodule in an attempt to improve localization prior to removal. This procedure usually takes place in the computerized tomography (CT) suite prior to the removal of the nodule. The patient is then transported to the surgical unit and the surgeon cuts down on the wire, uses a radionuclide detector, or uses visual landmarks to localize and remove the nodule.

A similar type of procedure is done to localize pulmonary nodules prior to resection. In some cases where pulmonary nodules may be difficult to locate at conventional open surgery or at thoracoscopy, a hook wire, injection of visible dye, or a radionuclide is place in or around the nodule in an attempt to improve localization prior to removal. This procedure usually takes place in the CT suite prior to the removal of the nodule. The patient is then transported to the surgical unit and the surgeon cuts down on the wire, uses a radionuclide detector, or uses visual landmarks to localize and remove the nodule.

In addition, the tools used during a medical procedure are also difficult to locate. For example, the location of a hand-held tool (e.g., a surgical stapler) utilized by a surgeon may not be known, other than intuitively by the surgeon. Any wired location sensor adds to the number of wires, tubes, etc. extending off from the hand-held tool—thereby reducing maneuverability of the tool.

Improved systems and methods are needed for tissue and tool localization for medical procedures performed in a variety of environments.

SUMMARY

The disclosure provides, in one aspect, a wireless localization system including an exciter coil, a sensor coil, a surgical tool including a head defining a longitudinal axis, and a first wireless tag coupled to the head at a first position along the longitudinal axis. The first wireless tag is configured to generate a first signal in response to a magnetic field generated by the exciter coil. The wireless localization system further includes a second wireless tag coupled to the head at a second position along the longitudinal axis. The second position is spaced from the first position. The second wireless tag is configured to generate a second signal in response to the magnetic field generated by the exciter coil. The wireless localization system further includes a processor that determines the location of the head based on the first signal and the second signal detected by the sensor coil.

In some embodiments, the system further includes a third wireless tag configured to generate a third signal in response to the magnetic field generated by the exciter coil. The processor determines the location of the head with respect to the third wireless tag based on the first signal, the second signal, and the third signal detected by the sensor coil.

In some embodiments, the processor determines an orientation of the head.

In some embodiments, the first wireless tag defines a first volume no greater than 60 mm$^3$, and the second wireless tag defines a second volume no greater than 60 mm$^3$.

In some embodiments, the first wireless tag includes a ferrite rod, a coil wound around the ferrite rod, and an integrated circuit chip in electrical communication with the coil.

In some embodiments, the first wireless tag includes a shell, and wherein the rod, the coil, and the integrated circuit chip are positioned within the shell.

In some embodiments, the system further includes a high magnetic permeability backing positioned within the shell.

In some embodiments, the first wireless tag includes an adhesive layer, and the first wireless tag is secured to the head with the adhesive layer.

In some embodiments, the first wireless tag includes a first coil and a second coil, wherein the first coil is spaced from the second coil along the longitudinal axis.

In some embodiments, the magnetic field generated by the exciter coil is within a range of 1 µT to 50 µT at a frequency within a range of 125 kHz to 150 kHz.

In some embodiments, the first wireless tag has an inductance value at the frequency within a range of 0.5 mH to 20 mH.

In some embodiments, the antenna has a quality factor within a range of 5 to 20, wherein the quality factor is defined as the ratio of inductive reactance to resistance at the frequency.

In some embodiments, the system further includes a user display including a perspective view of a virtual head shown at the location of the head.

In some embodiments, the user display includes a top-down view, a side view, an endoscopic camera view, or any combination thereof.

In some embodiments, the user display includes a partial spherical shell that indicates a relative position of the head with respect to a third wireless tag.

In some embodiments, the user display includes a shortest distance path extending between the virtual head and the partial spherical shell.

In some embodiments, the virtual head includes a marker to indicate the location the shortest distance path intersects the virtual head.

The disclosure provides, in one aspect, a device including a wireless probe with a first end and a second end opposite the first end, and a handle removably coupled to the second end of the wireless probe. The wireless probe generates a signal in response to a magnetic field and is localized based on the signal.

In some embodiments, the device further includes a flexible tether coupled to the wireless probe. The tether is positioned within the handle when the handle is coupled to the second end of the wireless probe.

In some embodiments, the wireless probe includes a plurality of markings along a length of the wireless probe.

In some embodiments, the wireless probe includes an axis that extends between the first end and the second end. The handle is aligned with the axis when the handle is coupled to the second end of the wireless probe.

In some embodiments, the device is configured for manual operation with the handle coupled to the wireless probe, manual operation with the wireless probe grasped by a surgical tool, and robotic operation with the handle removed from the wireless probe.

The disclosure provides, in one aspect, a device including a wireless tag and a spool including a mount portion. The spool is configured to be attached to a workspace by the mount portion. The device further includes a tether extending between the wireless tag and the spool.

In some embodiments, the mount portion includes an adhesive.

In some embodiments, the device further includes a clip configured to at least partially receive the wireless tag.

In some embodiments, the adhesive is positioned on a first side of the mount portion and the clip is positioned on a second side of the mount portion.

In some embodiments, the wireless tag includes a plurality of markings spaced along a length of the wireless tag.

In some embodiments, the plurality of markings is equally spaced along the length of the wireless tag.

In some embodiments, the wireless tag includes an aperture and the tether extends through the aperture.

The disclosure provides, in one aspect, a wireless tag applicator for a tool. The wireless tag applicator comprising a mount including a groove configured to receive at least a portion of the tool, a slide movable with respect to the mount along an application axis, and a wireless tag movable with the slide. The wireless tag includes an adhesive oriented toward the groove. The wireless tag is coupled to the tool in response to the slide moving along the application axis.

In some embodiments, the slide is a first slide and the wireless tag is a first wireless tag; and wherein the applicator further includes a second slide movable with respect to the mount along the application axis and a second wireless tag movable with the second slide.

In some embodiments, the second wireless tag is coupled to the tool in response to the second slide moving along the application axis.

In some embodiments, the tool is a surgical stapler and wherein the wireless tag is coupled to a side surface of a first jaw.

In some embodiments, the groove receives a portion of a second jaw of the surgical stapler.

In some embodiments, the slide includes a cavity that at least partially receives the wireless tag.

In some embodiments, the applicator further includes a magnet positioned within the cavity, and wherein the wireless tag includes a ferromagnetic rod.

In some embodiments, the cavity includes a notch and the wireless tag includes a shell with a protrusion positioned within the notch.

In some embodiments, the applicator further includes a removable backing coupled to the slide. The removable backing abuts the adhesive of the wireless tag.

In some embodiments, the removable backing includes a graspable portion, a first portion extending along a first axis from the graspable portion, a second portion extending along a second axis, and an arcuate portion positioned between the first portion and the second portion.

In some embodiments, the second axis is spaced apart and parallel to the first axis.

In some embodiments, the slide further includes a spring lever, and wherein the spring lever deflects in response to the slide moving along the application axis.

In some embodiments, the spring lever biases the slide away from the groove.

In some embodiments, the mount further includes a ramp portion and the slide includes a cam portion configured to slide relative to the ramp portion in response to the slide moving along the application axis.

In some embodiments, the wireless tag applicator generates an audible feedback in response to the slide moving along the application axis.

The disclosure provides, in one aspect, a method of aligning a virtual display perspective to a camera perspective. The method comprising: orienting a camera toward a region of interest with a first wireless tag positioned in the region of interest; positioning a second wireless tag within a field of view of the camera; determining a vector between the first wireless tag and the second wireless tag; and orienting the virtual display perspective with the vector.

In some embodiments, the camera is part of an endoscope.

In some embodiments, the region of interest is a chest cavity of a patient.

In some embodiments, positioning the second wireless tag within the field of view of the camera includes positioning the second wireless tag at a center of the field of view.

In some embodiments, positioning the second wireless tag within the field of view of the camera includes positioning the second wireless tag within a threshold distance from the camera.

In some embodiments, positioning the second wireless tag within the field of view of the camera does not require a specific orientation of the second wireless tag.

In some embodiments, determining the vector is in response to receiving a user input.

In some embodiments, determining the vector between the first wireless tag and the second wireless tag includes receiving a first signal from the first wireless tag in response to a magnetic field and receiving a second signal from the second wireless tag in response to the magnetic field.

Other aspects of the disclosure will become apparent by consideration of the detailed description and accompanying drawings.

Definitions

As used herein, the terms "processor" and "central processing unit" or "CPU" are used interchangeably and refer to a device that is able to read a program from a computer memory (e.g., ROM or other computer memory) and perform a set of steps according to the program. As used herein, the term "processor" (e.g., a microprocessor, a microcontroller, a processing unit, or other suitable programmable device) can include, among other things, a control unit, an arithmetic logic unit ("ALC"), and a plurality of registers, and can be implemented using a known computer architecture (e.g., a modified Harvard architecture, a von Neumann architecture, etc.). In some embodiments the processor is a microprocessor that can be configured to communicate in a stand-alone and/or a distributed environment, and can be configured to communicate via wired or wireless communications with other processors, where such one or more processor can be configured to operate on one or more processor-controlled devices that can be similar or different devices.

As used herein, the term "memory" is any memory storage and is a non-transitory computer readable medium. The memory can include, for example, a program storage area and the data storage area. The program storage area and the data storage area can include combinations of different types of memory, such as a ROM, a RAM (e.g., DRAM, SDRAM, etc.), EEPROM, flash memory, a hard disk, a SD card, or other suitable magnetic, optical, physical, or electronic memory devices. The processor can be connected to the memory and execute software instructions that are capable of being stored in a RAM of the memory (e.g., during execution), a ROM of the memory (e.g., on a generally permanent bases), or another non-transitory computer readable medium such as another memory or a disc. In some embodiments, the memory includes one or more processor-readable and accessible memory elements and/or components that can be internal to the processor-controlled device, external to the processor-controlled device, and can be accessed via a wired or wireless network. Software included in the implementation of the methods disclosed herein can be stored in the memory. The software includes, for example, firmware, one or more applications, program data, filters, rules, one or more program modules, and other executable instructions. For example, the processor can be configured to retrieve from the memory and execute, among other things, instructions related to the processes and methods described herein.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks, whether local or distant (e.g., cloud-based).

"About" and "approximately" are used to provide flexibility to a numerical range endpoint by providing that a given value may be "slightly above" or "slightly below" the endpoint without affecting the desired result.

The term "coupled," as used herein, is defined as "connected," although not necessarily directly, and not necessarily mechanically. The term coupled is to be understood to mean physically, magnetically, chemically, fluidly, electrically, or otherwise coupled, connected or linked and does not exclude the presence of intermediate elements between the coupled elements absent specific contrary language.

As used herein, the term "in electronic communication" refers to electrical devices (e.g., computers, processors, etc.) that are configured to communicate with one another through direct or indirect signaling. Likewise, a computer configured to transmit (e.g., through cables, wires, infrared signals, telephone lines, airwaves, etc.) information to another computer or device, is in electronic communication with the other computer or device.

As used herein, the term "transmitting" refers to the movement of information (e.g., data) from one location to another (e.g., from one device to another) using any suitable means.

As used herein, the term "network" generally refers to any suitable electronic network including, but not limited to, a wide area network ("WAN") (e.g., a TCP/IP based network), a local area network ("LAN"), a neighborhood area network ("NAN"), a home area network ("HAN"), or personal area network ("PAN") employing any of a variety of communications protocols, such as Wi-Fi, Bluetooth, ZigBee, etc. In some embodiments, the network is a cellular network, such as, for example, a Global System for Mobile Communications ("GSM") network, a General Packet Radio Service ("GPRS") network, an Evolution-Data Optimized ("EV-DO") network, an Enhanced Data Rates for GSM Evolution ("EDGE") network, a 3GSM network, a 4GSM network, a 5G New Radio, a Digital Enhanced Cordless Telecommunications ("DECT") network, a digital AMPS ("IS-136/TDMA") network, or an Integrated Digital Enhanced Network ("iDEN") network, etc.

As used herein, the term "subject" or "patient" refers to any animal (e.g., a mammal), including, but not limited to, humans, non-human primates, companion animals, livestock, equines, rodents, and the like, which is to be the recipient of a particular treatment. Typically, the terms "subject" and "patient" are used interchangeably herein in reference to a human subject.

As used herein, the term "subject/patient suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass) but for whom the stage of cancer is not known. The term further includes people who once had cancer (e.g., an individual in remission).

As used herein, the term "biopsy tissue" refers to a sample of tissue (e.g., breast tissue) that is removed from a subject for the purpose of determining if the sample contains cancerous tissue. In some embodiments, biopsy tissue is obtained because a subject is suspected of having cancer. The biopsy tissue is then examined (e.g., by microscopy; by molecular testing) for the presence or absence of cancer.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include tissue, blood products, such as plasma, serum and the like. Such examples are not however to be construed as limiting the sample types applicable to the present invention.

As used herein, the term "tag," "marker tag," "wireless tag," or "SmartClip®" refers to the small marker that, when excited by an exciter's time varying magnetic field, will emit a "homing beacon" spectrum of frequency(ies) received by the "sensor coil(s)" or "witness coil(s)" and used to determine its location. It may be programmed to produce a unique spectrum, thus permitting multiple tags to be located simultaneously.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

In the foregoing description of preferred embodiments, specific terminology has been resorted to for the sake of clarity. However, the invention is not intended to be limited to the specific terms so selected, and it is to be understood that each specific term includes all technical equivalents which operate in a similar manner to accomplish a similar technical purpose. Terms such as "top" and "bottom", "front" and "rear", "inner" and "outer", "above", "below", "upper", "lower", "vertical", "horizontal", "upright" and the like are used as words of convenience to provide reference points.

BRIEF DESCRIPTION OF THE DRAWINGS

FIG. 8 is a side view of a device including a wireless probe and a detachable handle.

FIG. 9 is a side view of the device of FIG. 8.

Before any embodiments are explained in detail, it is to be understood that the invention is not limited in its application to the details of construction and the arrangement of components set forth in the following description or illustrated in the following drawings. The invention is capable of other embodiments and of being practiced or of being carried out in various ways.

DETAILED DESCRIPTION

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

Provided herein are systems, devices, assemblies, and methods for integrating a remotely located tag into medical procedures. While the specification focuses on medical uses in human tissues, it should be understood that the systems and methods find broader use, including non-human uses (e.g., use with non-human animals such as livestock companion animals, wild animals, or any veterinary settings). For example, the systems may be used in environmental settings, agricultural settings, industrial settings, or the like.

In addition to being located within human tissue, wireless tags can be integrated into tools to wirelessly track the location and orientation of tools utilized in various medical procedures. Such a wireless localization system is detailed in U.S. patent application Ser. No. 17/746,105, filed May 17, 2022, incorporated herein by reference in its entirety.

Figure 22:
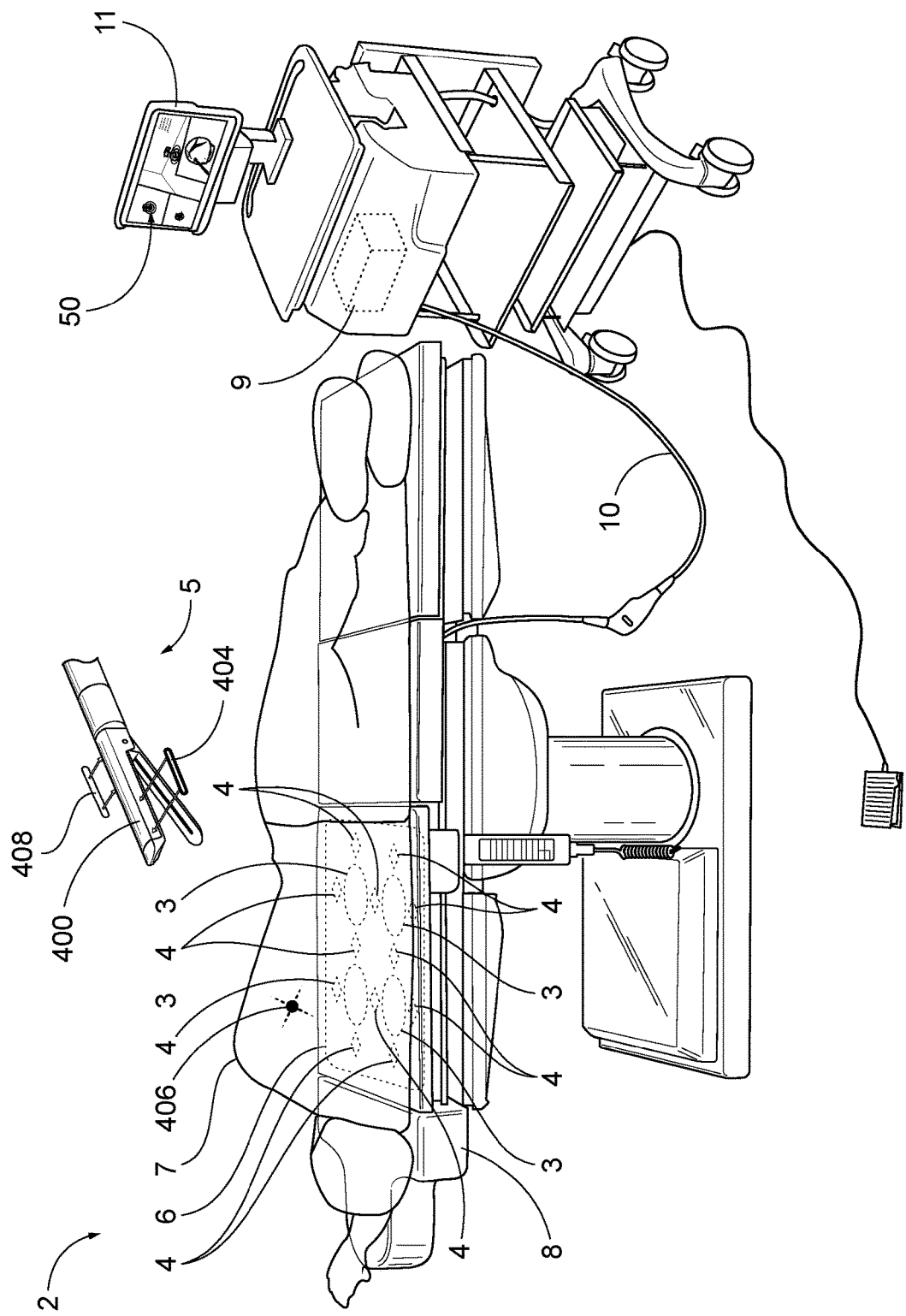
FIG. 22 is a schematic view of a wireless localization system.

With reference to FIG. 22, the present disclosure provides a wireless localization system 2 including an exciter coil 3, a sensor coil 4, and a tool 5 (e.g., a surgical stapler, a surgical tool, a robotic tool). In the illustrated embodiment, the exciter coil 3 and the sensor coil 4 are positioned within a pad 6 that is position under a patient 7. In the illustrated embodiment, the pad 6 is positioned within a surgical table 8. Such a pad is detailed further in U.S. patent application Ser. No. 17/746,105, filed May 17, 2022, incorporated herein by reference in its entirety.

Figure 14:
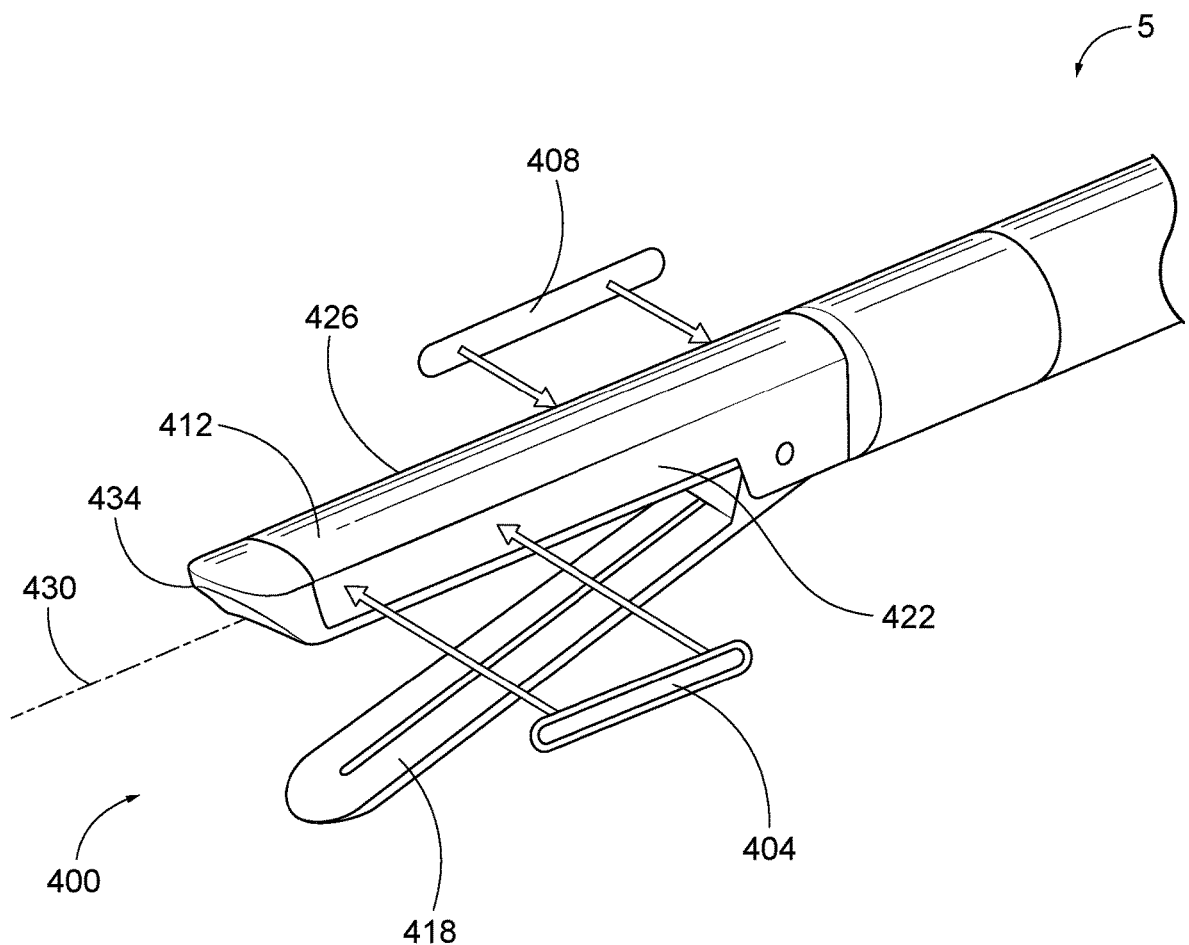
FIG. 14 is a perspective view surgical stapler including wireless tags.

With reference to FIG. 14, in the illustrated embodiment, a first wireless tag 404 and a second wireless tag 408 are coupled to the tool 5. In particular, the surgical tool 5 includes a head 400 defining a longitudinal axis 430. In the illustrated embodiment, the head 400 defines a terminal end 434 of the surgical tool 5. In the illustrated embodiment, the tracked tool 400 is a surgical stapler.

With continued reference to FIG. 14, the first wireless tag 404 is coupled to the head 400 at a first position along the longitudinal axis 430. The first wireless tag 404 generates a first signal in response to a magnetic field generated by the exciter coil 3. The second wireless tag 408 is coupled to the head 400 at a second position along the longitudinal axis 430. The second position is spaced from the first position. In some embodiments, the first wireless tag 404 partially overlaps the second wireless tag 408 along the longitudinal axis 430. The second wireless tag 408 generates a second signal in response to the magnetic field generated by the exciter coil 3. In other words, the wireless tags 404, 408 are configured to generate a signal in response to a magnetic field generated by at least one exciter coil 3.

With continued reference to FIG. 14, the surgical stapler includes a first jaw 412 (e.g., a reload jaw) and a second jaw 418 (e.g., an anvil jaw). The first wireless tag 404 is coupled to a first side 422 of the first jaw 412 and the second wireless tag 408 is coupled to a second side 426 of the first jaw 412, opposite the first side 422. In the illustrated embodiment, the first wireless tag 404 is offset from the second wireless tag 408 along the axis 430 of the first jaw 412. In other words, the first wireless tag 404 is positioned a first distance to the distal tip 434 of the first jaw 412 and the second wireless tag 408 is positioned a second distance to the distal tip 434, where the first distance is shorter than the second distance. In the illustrated embodiment, the wireless tags 404, 408 are applied to locations on the tool 400 such that the wireless tags do not impact the ability of the tool to pass through a port (e.g., port compatibility of the surgical tool remains unchanged by the addition of wireless tags).

With continued reference to FIG. 22, signals generated by the wireless tags 404, 408 are detected by at least one sensor coil 4. The system 2 further includes a processor 9 configured to determine the location of the tool 5 based on the signals detected by the sensor coil 4. In some embodiments, the processor 9 is configured to determine the orientation (or orientations) and location of the tool 5 (e.g., localization in six degrees-of-freedom, 6DOF). In the illustrated embodiment, the processor 9 is electrically coupled to the pad 6 by a wired connection 10. In some embodiments, the processor 9 controls the magnetic field generated by the exciter coils 2 and receives the signals detected by the sensor coils 4.

In some embodiments, the system 2 further includes a third wireless tag 406 that generates a third signal in response to the magnetic field generated by the exciter coil 3. In some embodiments, the third wireless tag 408 is implanted within a patient. The processor 9 is configured to determine the location of the tool 5 with respect to the implanted wireless tag 406 based on the signals detected by the sensor coil 4. In other words, the processor 9 determines the location of the tool head 400 and the orientation of the tool head 400 with respect to the third wireless tag 406 based on the signals detected by the sensor coil 4.

Simultaneously tracking the location and orientation of both a surgical stapler and a wireless tag implanted in or on a patient has advantages. Given that the implanted wireless tag marks the target location (e.g., of the cancer, etc.), the margin of tissue from the target location can be confirmed after the stapler jaws have been closed (and after re-arrangement of the tissue caused by the stapler closure). In other words, before the stapler engages and cuts tissue, the positioning and margin is confirmed by a wireless localization system presented herein. If necessary, the stapler can be moved and reclosed before a cut occurs. Therefore, the margin can be confirmed with high confidence.

Surgical staplers are designed to fit through a port with limited space and clearance. It is challenging to design and manufacture staplers of small diameter, and staplers typically do not have extra space relative to the port. For example, a SureForm 45 stapler available from Intuitive Surgical is designed to pass through a 12 mm port, and there is little clearance between the stapler head and the port.

In some embodiments, the wireless localization system disclosed herein estimates the position and orientation of the stapler head from the shaft position and kinematic data coming from the device that controls or monitors the stapler head articulation. It is advantageous to track the stapler head itself instead of just tracking the stapler shaft outside the port, because the stapler head can articulate in various directions. Furthermore, tracking the location of the stapler head directly would require less integration and software implantation, validation, and communications.

Figure 1:
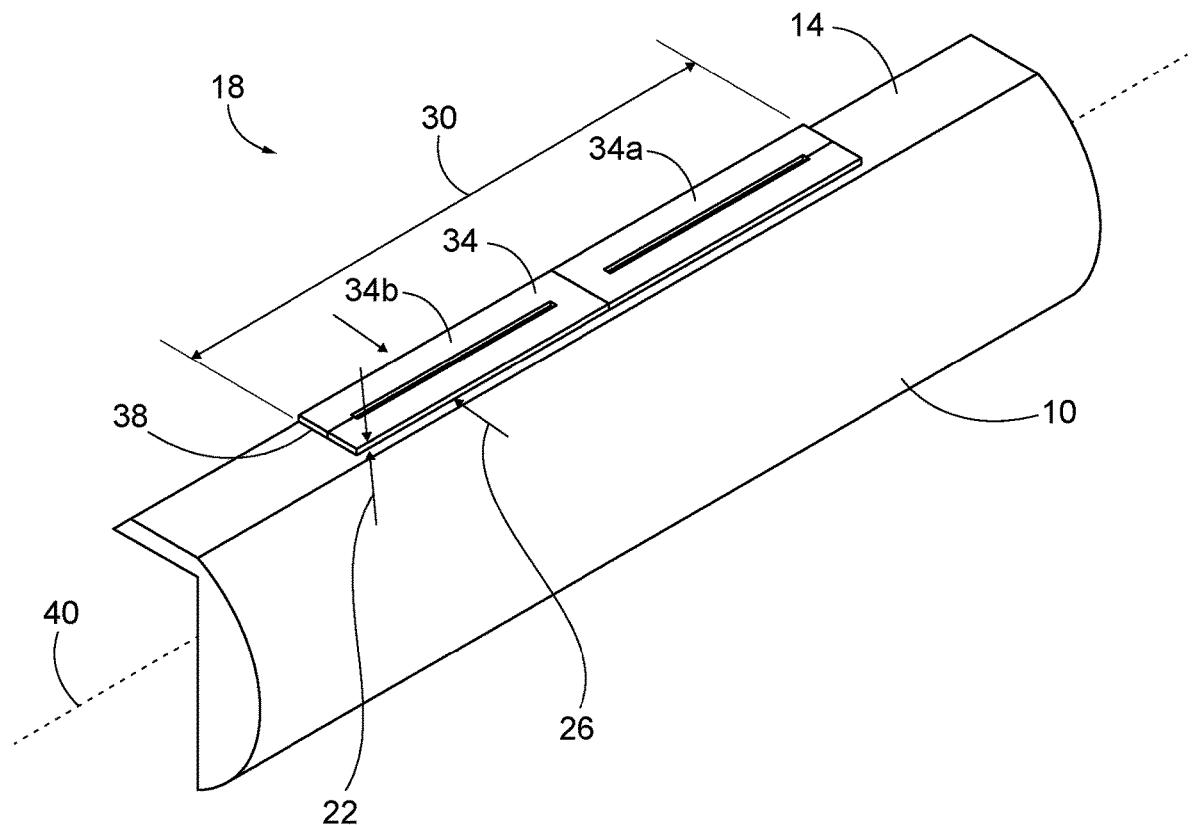
FIG. 1 is a perspective view of an antenna coupled to a portion of a surgical stapler.

With reference to FIG. 1, a stapler head 12 (e.g., a head of the SureForm 45 stapler) has a narrow portion 14 where a wireless tag 18 is mounted. In some embodiments, the wireless tag 18 is coupled to the narrow portion 14 with an adhesive. In the illustrated embodiment, the wireless tag 18 has a thickness 22 within a range of approximately 0.3 mm to approximately 0.8 mm. In the illustrated embodiment, the wireless tag 18 has a width 26 within a range of approximately 2 mm to approximately 4 mm. In some embodiments, the wireless tag 18 has a length 30 of approximately 30 mm. In some embodiments, the wireless tag 18 defines a volume no greater than 60 $mm^3$. In other embodiments, the wireless tag 18 defines a volume no greater than 38 $mm^3$. In some embodiments, the thickness 22 of the wireless tag 18 is approximately 0.35 mm, the width 26 is approximately 3.5 mm, and the length 30 is approximately 30 mm. In other embodiments, the thickness 22 of the wireless tag 18 is approximately 0.75 mm, the width 26 is approximately 2.5 mm, and the length 30 is approximately 30 mm.

With continued reference to FIG. 1, in the illustrated embodiment, the wireless tag 18 includes an antenna 34 and a backing 38. In the illustrated embodiment, the antenna 34 includes a first coil 34A and a second coil 34B. The first coil 34A is spaced from the second coil 34B. In the illustrated embodiment, the first coil 34A is spaced from the second coil 34B along a longitudinal axis 38 of the tool 10 (e.g., the stapler head longitudinal axis). In the illustrated embodiment, the first coil 34 and the second coil 34B are positioned the same distance from a longitudinal axis 40 of the stapler 12. To achieve high inductance, thin wire is utilized for the coils 34A, 34B and as many turns as possible within the volume constraints are wound. In some embodiments, each of the coils 34A, 34B has approximately 100-150 turns. In some embodiments, each of the coils 34A, 34B has approximately 250-350 turns.

In the illustrated embodiment, the wireless tag 18 includes dual coil antenna 34 with a high magnetic permeability, low electrical conductivity material backing 38. In some embodiments, the backing 38 is Flux Field Directional Material (FFDM) EM25TP available from 3M™. In some embodiments, the backing 38 has a relative permeability (μ') of approximately 2000.

Even with the small space constraints, the antenna 34 is capable of gathering enough power from a transmitted magnetic field from an exciter coil to power up and generate a signal. In some embodiments, the magnetic field generated by the exciter coil 3 is within a range of approximately 1 μT to approximately 50 μT at a frequency within a range of approximately 125 kHz to approximately 150 kHz. In some embodiments, the antenna transmits a signal at a frequency offset from the original transmitted signal.

In some embodiments, the wireless tag 18 (e.g., antenna, backing, etc.) has an inductance value at the frequency within a range of approximately 0.5 mH to approximately 20 mH. In some embodiments, the wireless tag 18 has a quality factor (Q) (e.g., the ratio of inductive reactance to resistance at a frequency) within a range of approximately 5 to approximately 20. A higher quality factor (Q) will reduce the bandwidth of the wireless tag 18 and a lower quality factor will produce insufficient signal. A lower inductance will produce inadequate voltage to power the wireless tag, and a higher inductance will reduce the field produced. To power the wireless tag 18, the antenna 34 needs sufficient inductance to result in an adequate voltage and needs to have a high quality factor (e.g., high ratio of power stored in the circuit per cycle to power dissipated in the circuit per cycle). Furthermore, the antenna 34 must function in close proximity to metal because staplers, for example, are in general metallic.

Figure 2:
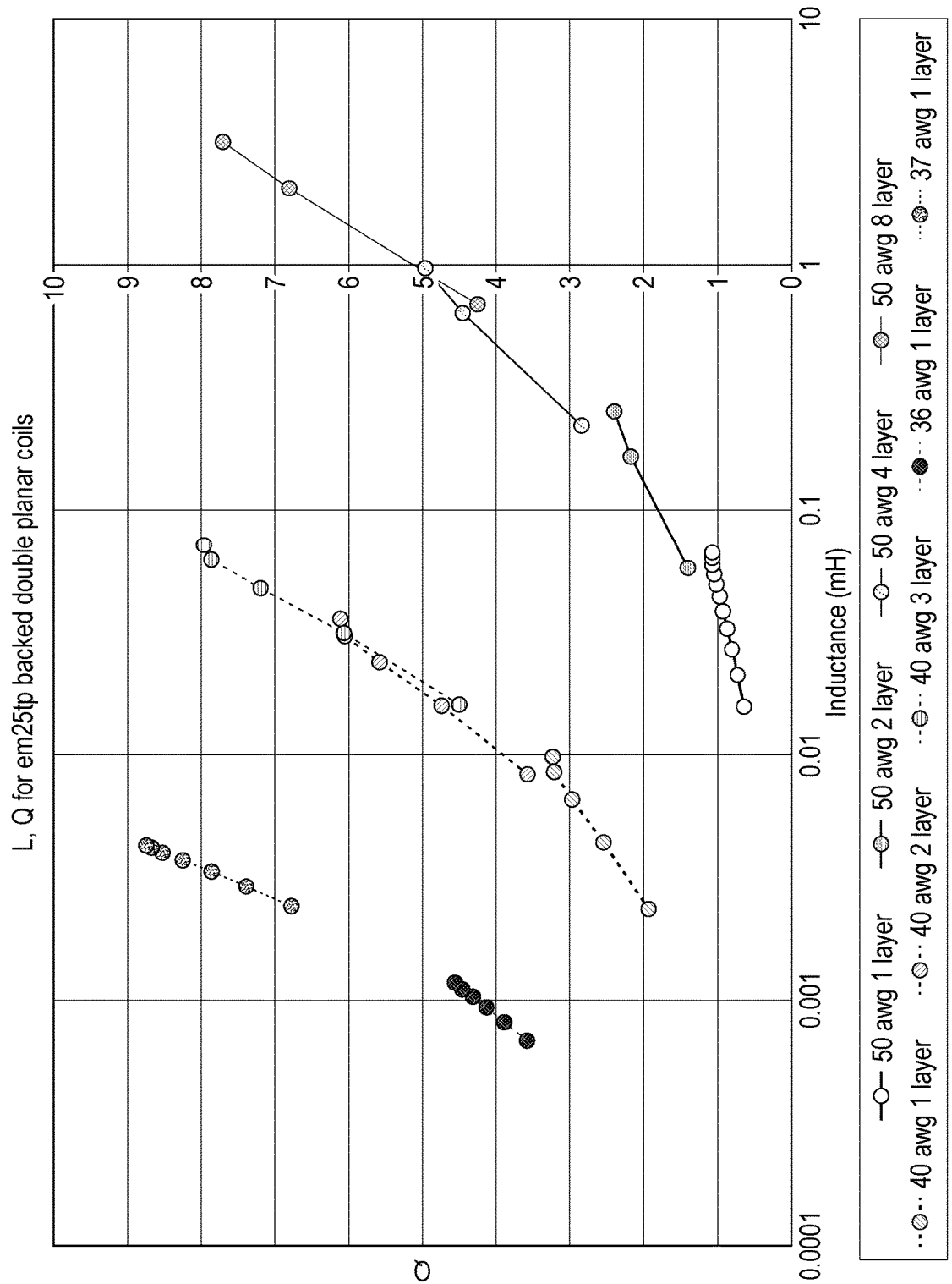
FIG. 2 is a graph of modeled Q and inductance values for different winding configurations for the antenna of FIG. 1.

With reference to FIG. 2, modeling results for various configurations are illustrated. Specifically, the quality factor (Q) and the inductance of different configurations of windings are illustrated. In some embodiments, the Q is approximately 7.7 and the inductance is approximately 3.15 mH. In another embodiment, the Q is approximately 9.4 and the inductance is approximately 3.6 mH.

As detailed herein, the system 2 wirelessly tracks the tool 5 (e.g., a robotic surgical stapler, a manual surgical stapler) with a low-profile wireless tag (e.g., wireless tag 404, wireless tag 408, wireless tag 18, etc.) that is adhered to the stapler head 400 without impacting the ability of the stapler to pass through the surgical port.

Figure 3:
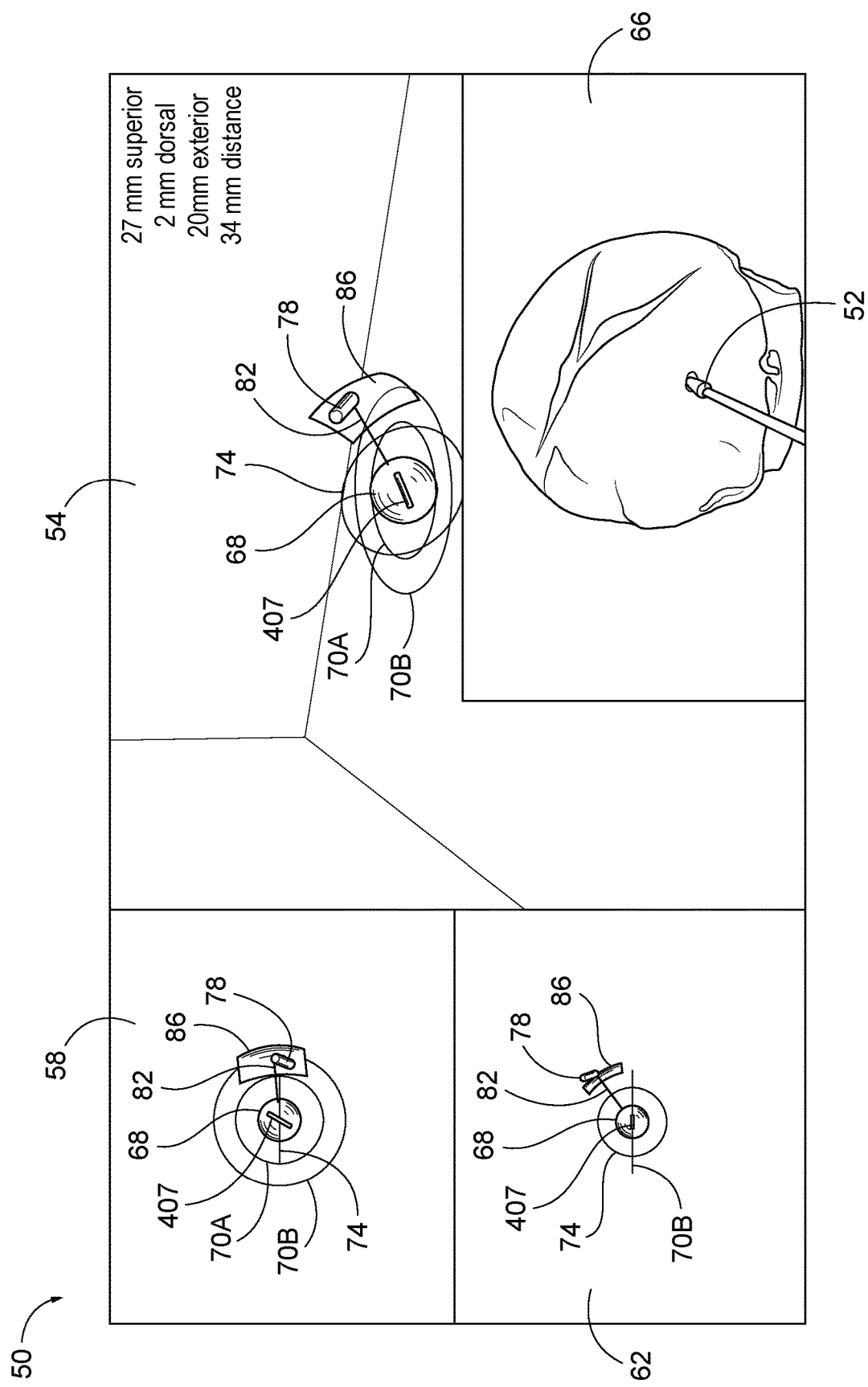
FIG. 3 is a schematic of a navigation display for locating a wireless tag embedded in a body with respect to a tracked probe.

With reference to FIG. 22, the system 2 further includes a display 11 (e.g., a monitor) showing a user display 50. With reference to FIG. 3, the user display 50 including a perspective view 54 of localization of a tool 52 (e.g., a wireless probe). In the illustrated embodiment, the user display 50 also includes a top-down view 58, a side view 62, and an endoscopic camera view 66 (e.g., a display drawn from a similar perspective as that of the endoscopic camera). The endoscopic camera view 66 can be on a separate screen or overlaid on the same screen as the views 54, 58, 62. In some embodiments, the user display 50 includes a perspective view, a top-down view, a side view, an endoscopic camera view, or any combination thereof.

Figure 5A:
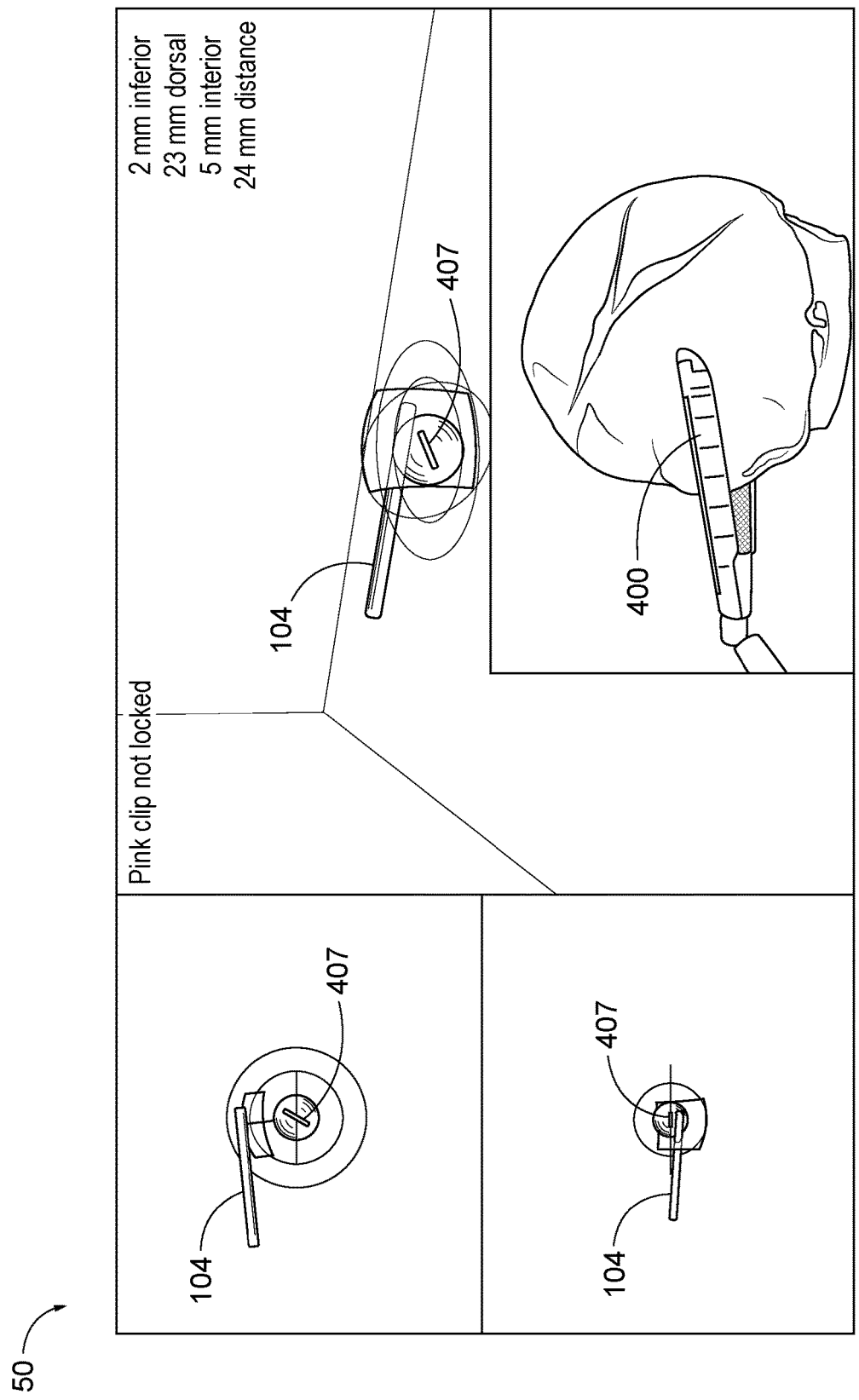
FIG. 5A is a schematic of a navigation display with a surgical stapler wirelessly localized relative to the wireless tag embedded in the body.

With continued reference to FIG. 3, the user display 50 illustrates a wireless tag illustration 407 corresponding to the location of the physical wireless tag 406 implanted in the patient 7 (e.g., in a patient lung). In the illustrated embodiment, the wireless tag illustration 407 is positioned within a sphere 68. In some embodiments, the sphere 68 is a user-defined margin around the implanted wireless tag 406. In the illustrated embodiment, the views 54, 58, 62 include two rings 70A, 70B for the X-Y plane and one ring 74 for the Y-Z plane. The user display 50 simultaneously illustrates in real-time the tracked tool 52. In the illustrated embodiment, the tracked tool 52 is represented virtually as a cylinder 78 in the user display 50. In some embodiments, the tracked tool 52 is a wired probe configured for interrogating an area (FIG. 3). In other embodiments, the tracked tool is a wirelessly localized stapler (FIG. 5A). A line 82 illustrates the shortest path between the tracked tool 52 and the sphere 68 of the implanted wireless tag 406. The user display 50 further includes a spherical shell 86 that indicates a relative position of the tool 52 with respect to the implanted wireless tag 406.

Figure 4A:
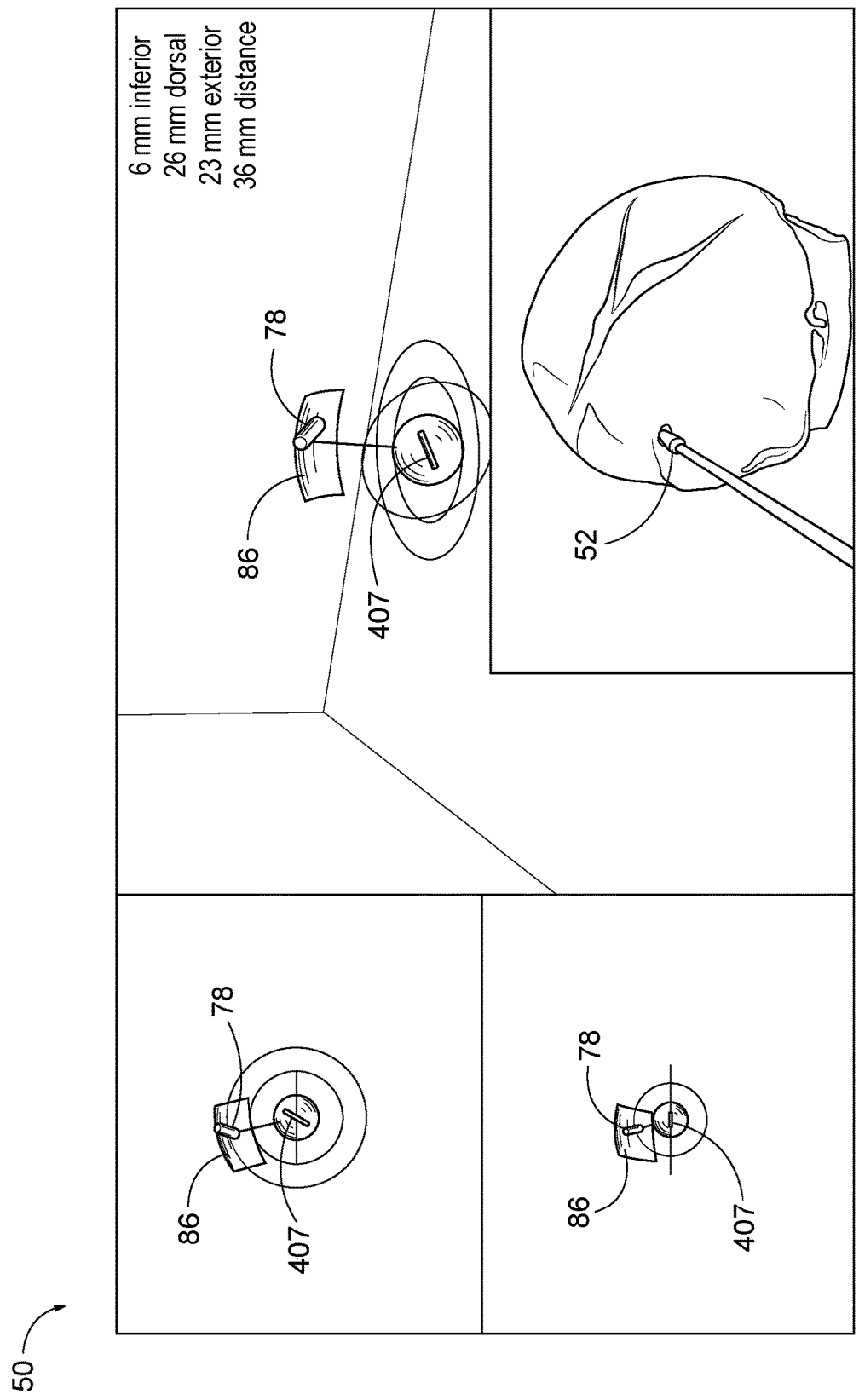
FIGS. 4A-4C are schematics of navigation displays with a tracked probe in positions relative to the wireless tag embedded in the body.
Figure 4B:
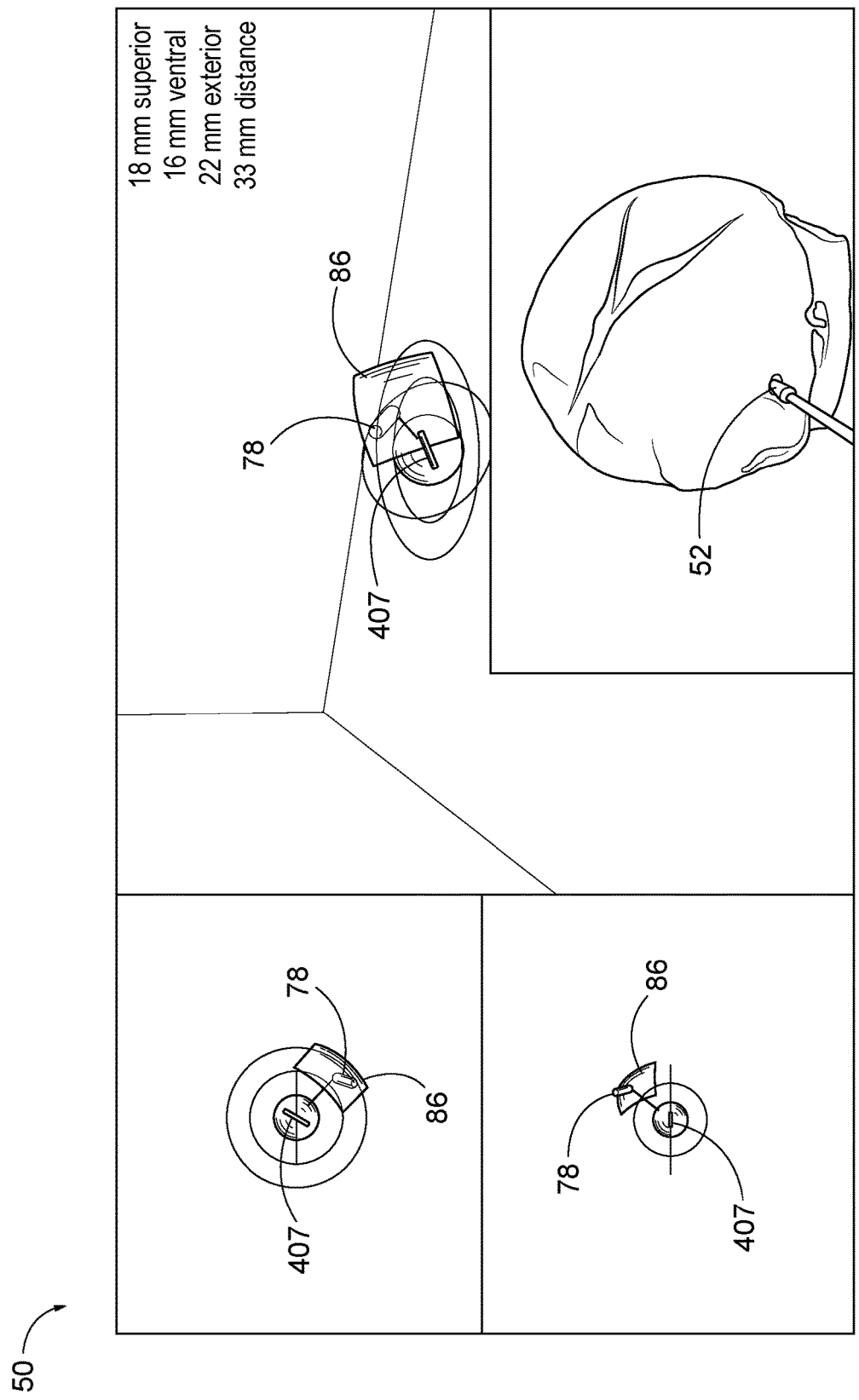
Figure 4C:
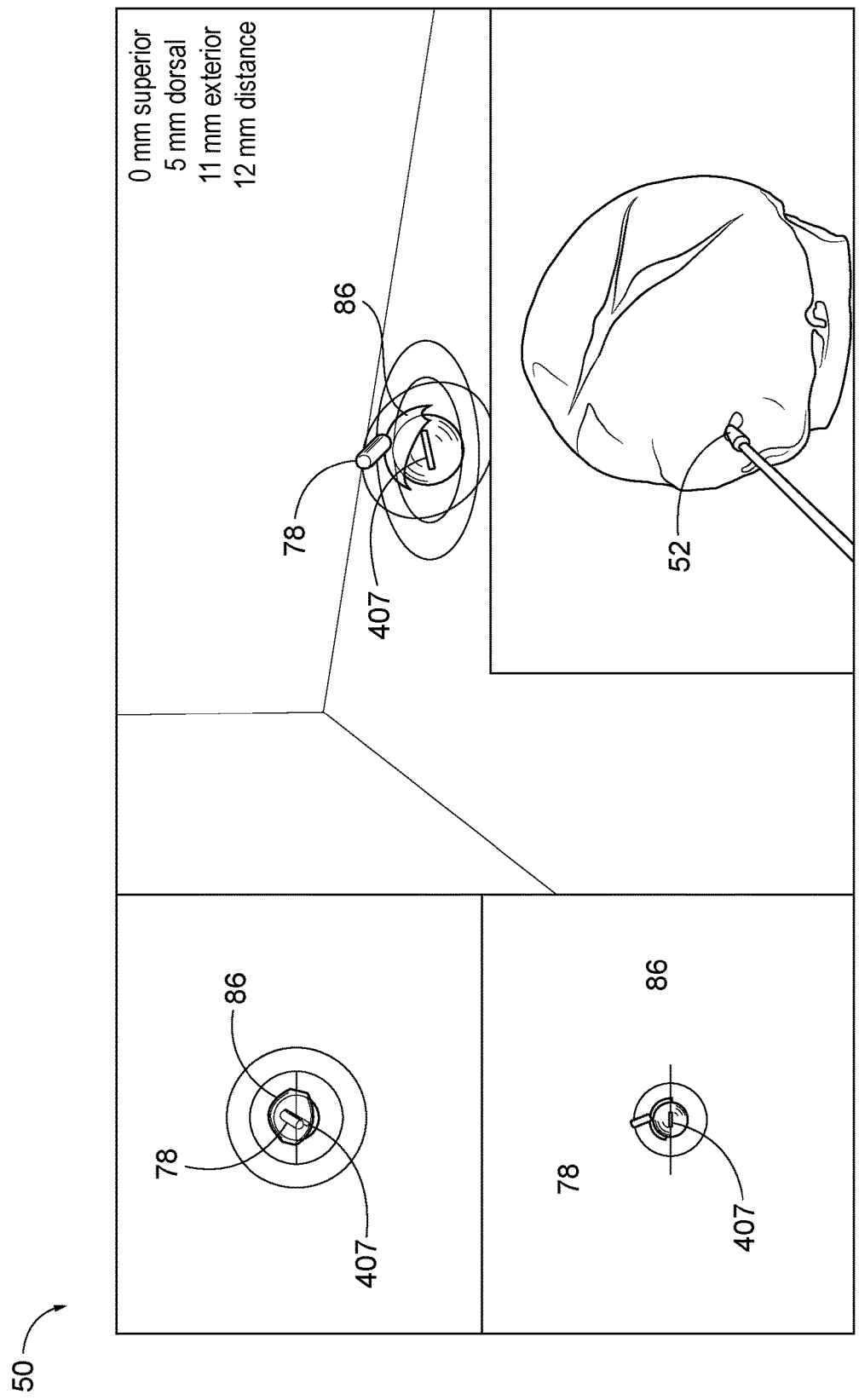

With reference to FIGS. 4A, 4B, and 4C, the spherical shell 86 indicates a relative position of the tool 52 with respect to the implanted wireless tag 406. In other words, the spherical shell 86 provides context to allow the user looking at the display 50 to understand the relative position of the tool 52 with respect to the implanted wireless tag 406, without referencing multiple views. In some embodiments, the spherical shell 86 increases in size as the distance between the tool 52 and the implanted wireless tag 406 increases. With reference to FIG. 4C, when the tracked tool 52 is close to the targeted implanted wireless tag 406, the curvature of the spherical shell 86 increases, and the segment appears to wrap around the target sphere 68.

Figure 5B:
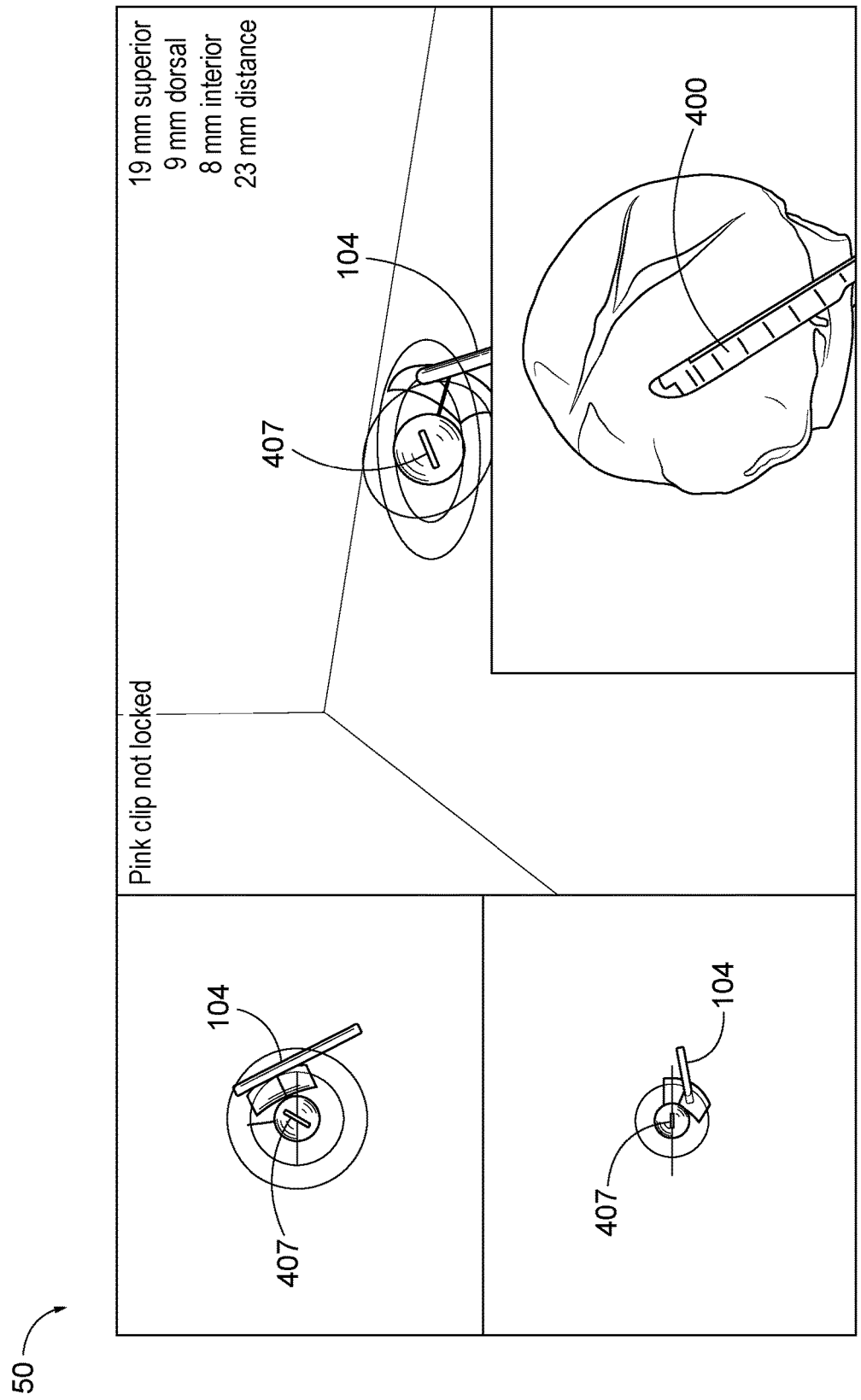
FIG. 5B is a schematic of a navigation display with the surgical stapler of FIG. 5A in a closed or clamped configuration.

In some embodiments, the color of the spherical shell 86 indicates to a user looking at the display 50 which side of the spherical shell 86 (inner or outer) is facing the observer. In some embodiments, multiple sphere shells (each with different size or color) is used to display multiple tracked tools simultaneously. In some embodiments, the spherical shell 86 color is light blue when the inner surface of the sphere is viewed by the observer. This, along with the curvature, indicates to the user that the tracked tool 52 is behind the implanted wireless tag 406 (FIG. 4A), from viewing just the perspective view 54, without having to consult the top-down view 58, for example. In some embodiments, the spherical shell 86 color is light purple when the outer surface of the sphere is viewed by the observer. This, along with the curvature, indicates to the user that the tracked tool 52 is in front of the implanted wireless tag 406 (FIG. 4B), from just the perspective view 54, without having to consult the top-down view 58, for example, With reference to FIGS. 5A-5B, the localization of the stapler head 400 with respect to the implanted wireless tag 406 is illustrated in the user display 50—with the stapler head 400 virtually represented as a cylinder 104. In the illustrated embodiment, the cylinder 104 length is identical to the length of the stapler head 400. In FIG. 5A, the jaws of the stapler head 400 are open. In FIG. 5B, the jaws of the stapler head 404 are closed. With the stapler jaws closed, the user can advantageously confirm the location of the stapler head 404 relative to the implanted wireless tag 406 before cutting any tissue. In other words, tissue may move as the stapler jaws close and the display 50 illustrates the relative position of the stapler head 400 relative to the implanted wireless tag 406 after the stapler jaws are closed.

Figure 6:
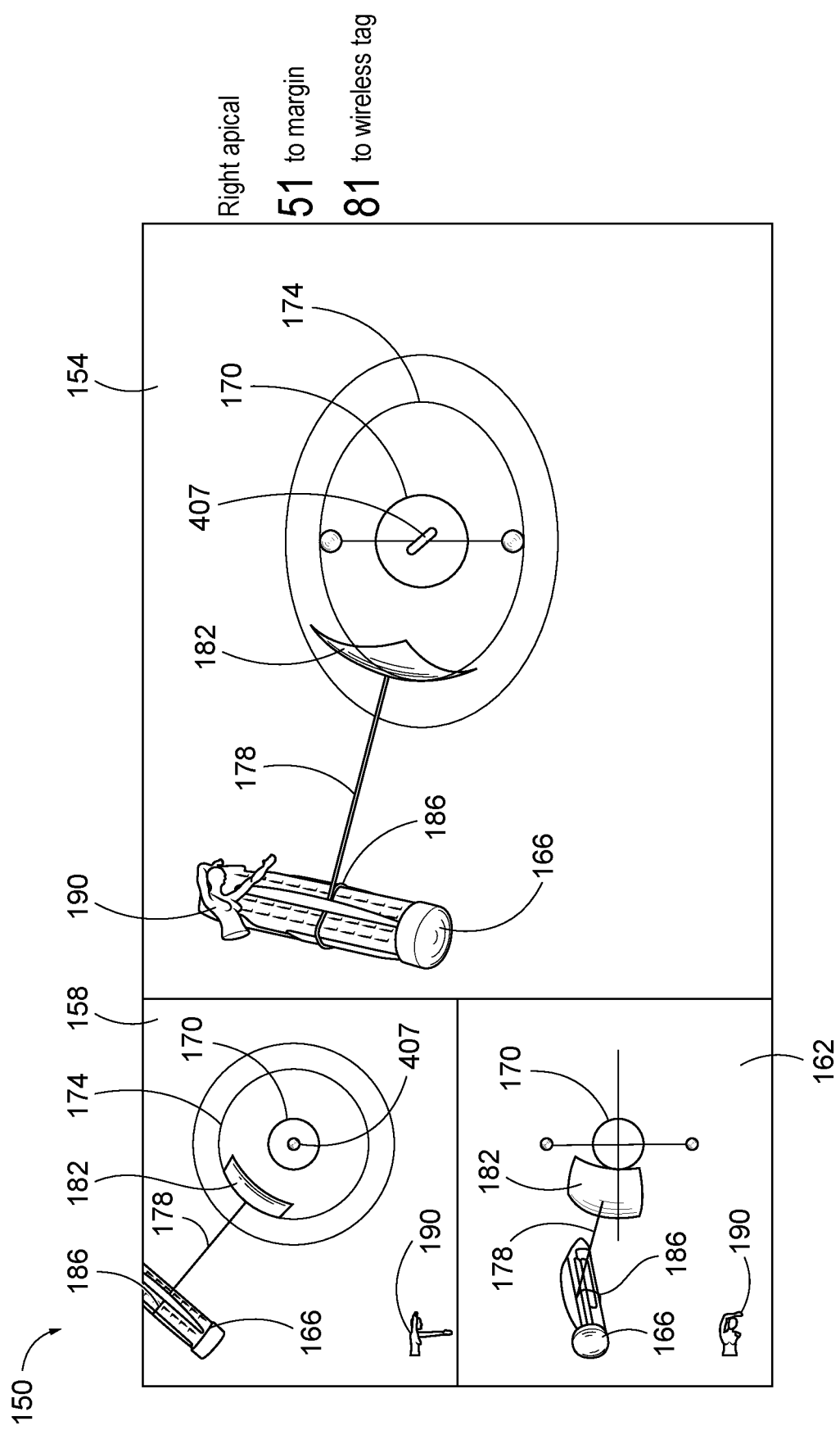
FIG. 6 is a navigation display with a surgical stapler wirelessly localized relative to a wireless tag.

With reference to FIG. 6, a user display 150 is illustrated with a perspective view 154, a top-down view 158, and a side view 162 showing a virtual head representation 166 (e.g., a virtual head corresponding to the location of the physical stapler head 400) relative to a virtual tag representation 407 (e.g., a virtual tag corresponding to the location of the physical wireless tag 406) implanted in the patient 7. The user display 150 includes a first user-defined volume 170 (e.g., sphere) positioned around the wireless tag representation 407 (e.g., to indicate a size and shape of a tumor), and a second user-defined volume 174 (e.g., a sphere) positioned around the first user-defined volume 170 (e.g., to represent a desired margin from the tumor). in some embodiments, the user-defined volumes 170, 174 are not spherical. The user display 150 further includes a shortest distance path 178 extending between the virtual head representation 166 (e.g., virtual head) and a partial spherical shell 182. In some embodiments, the partial spherical shell 182 operates similarly to the spherical shell 86 of the user display 50 discussed herein. The user display 150 further includes a marker 186 positioned on the virtual head 166 to indicate the location at which the shortest distance path 178 intersects the virtual head 166. In other words, the marker 186 identifies what portion of the head 400 is closest to the wireless tag 406. In the illustrated embodiment, the marker 186 is a ring wrapped around the virtual head representation 166. In some embodiments, the user display 150 includes a virtual patient 190 representing the orientation of the patient 7 in any given view (e.g., views 154, 158, 162).

Figure 7:
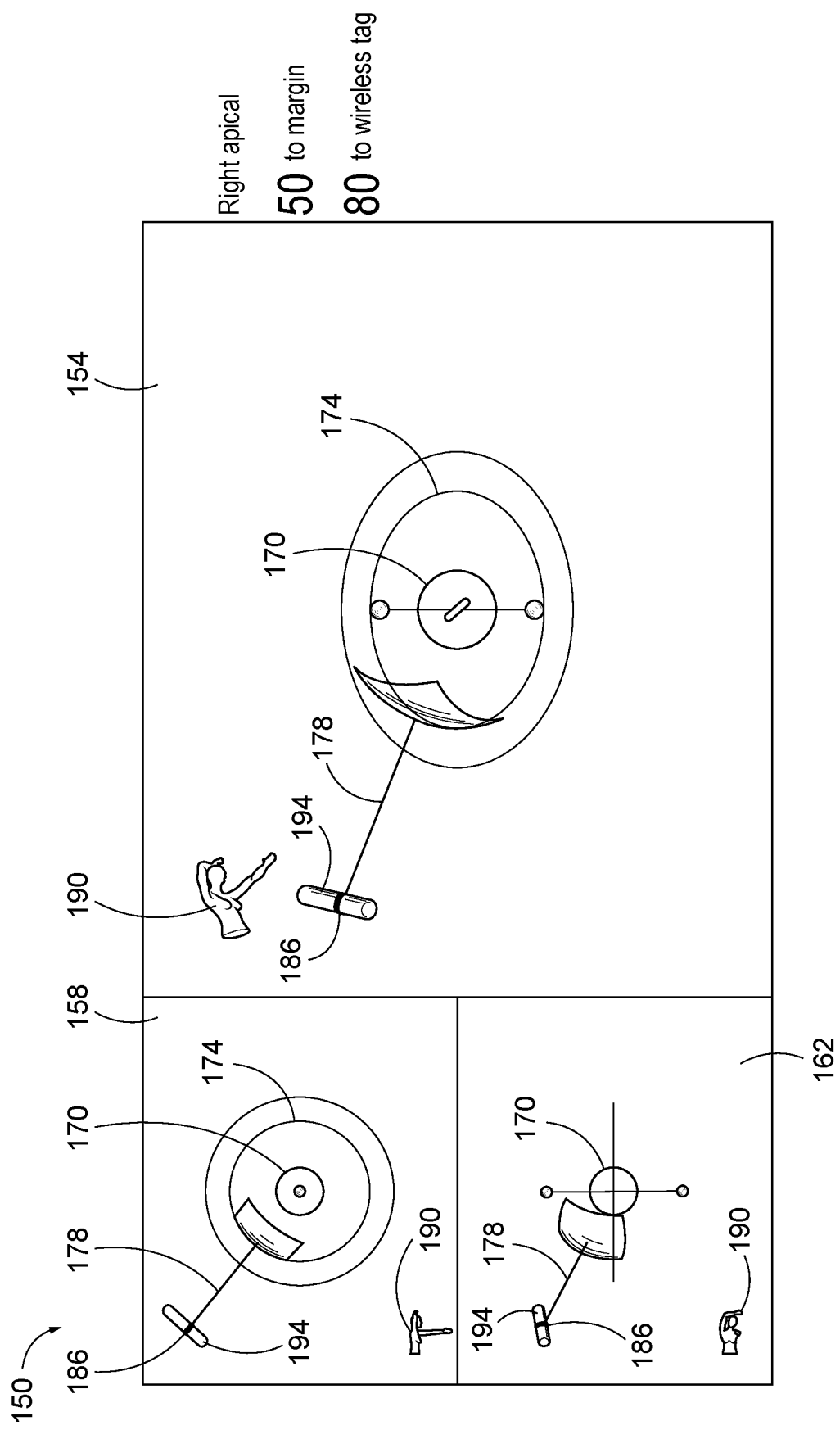
FIG. 7 is a navigation display with a tracked probe wirelessly localized relative to a wireless tag.

With reference to FIG. 7, the user display 150 is showing with a virtual wireless probe representation 194 (e.g., virtual tag corresponding to the location of a physical wireless probe 204, FIG. 8) relative to the virtual tag representation 407 (e.g., virtual tag corresponding to the location of the physical wireless tag 406) implanted in the patient 7. In some embodiments, the user display 150 toggles between visualizing the position and orientation of the tracked wireless tag (FIG. 7) and visualizing the position and orientation of the tracked stapler (FIG. 6).

In some embodiments, the user display is presented within a robotic console and/or drawn from nearly the same perspective as the endoscope view. In some embodiments, the wireless localization system subscribes to a robotic positioning stream to determine the endoscopic camera point of view. In some embodiment, the user display point of view is configured to correspond to the endoscopic view. In some embodiment, two video outputs to the robotic console are simultaneously presented to the user to provide a stereoscopic 3D view.

Figure 21:
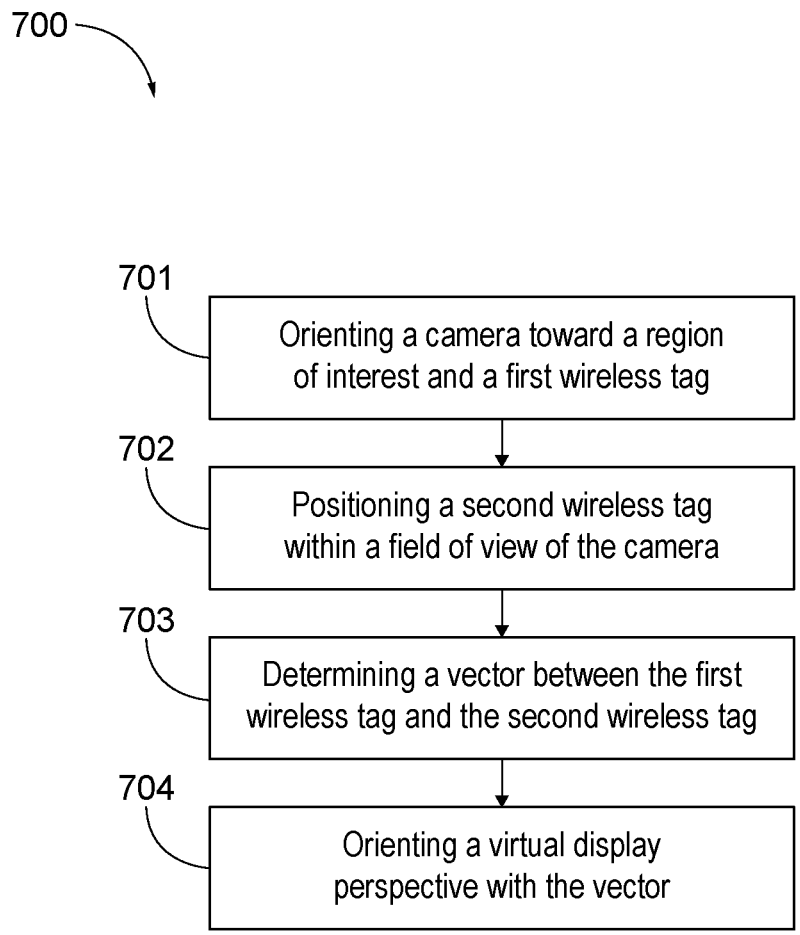
FIG. 21 is a flowchart of a method of aligning a virtual display perspective to a camera perspective.

With reference to FIG. 21, a method 700 of aligning a virtual display (e.g., display 150, display 50, etc.) to a camera perspective (e.g., an endoscopic camera perspective) is illustrated. The method 700 includes (STEP 701) orienting a camera (e.g., an endoscopic camera) toward a region of interest with a first wireless tag position in the region of interest. In some embodiments, the camera is part of an endoscope. In some embodiments, the camera is part of a robotic surgical system. In some embodiments, the region of interest is a chest cavity of a patient. The method 700 further includes (STEP 702) positioning a second wireless tag within a field of view of the camera. In some embodiments, positioning the second wireless tag within the field of view of the camera includes positioning the second wireless tag at a center of the field of view. In some embodiments, positioning the second wireless tag within the field of view of the camera includes positioning the second wireless tag within a threshold distance from the camera. In some embodiments, the threshold distance is approximately 6 inches. In other embodiments, the threshold distance is approximately 1 inch. In some embodiments, the threshold distance is within a range from approximately 1 inch to approximately 6 inches. Advantageously, positioning the second wireless tag within the field of view of the camera does not require a specific orientation of the second wireless tag.

The method 700 further includes (STEP 703) determining a vector between the first wireless tag and the second wireless tag, and (STEP 704) orienting the virtual display perspective view the vector. In some embodiments, determining the vector is in response to receiving a user input (e.g., a button press). In some embodiments, determining the vector between the first wireless tag and the second wireless tag includes receiving a first signal from the first wireless tag in response to a magnetic field and receiving a second signal from the second wireless tag in response to the magnetic field.

In one embodiment, the camera alignment method for an endoscopic procedure is summarized as follows: (a) the user orients the endoscope such that the expected position of the tumor is roughly centered in the endoscope display; (b) the user then inserts the probe into the chest cavity (if not already present); (c) the user moves the probe as close to the endoscope lens as reasonable and centers the probe in the endoscope display. Orientation of the probe does not have impact in this process; (d) the user presses a software button to direct they system to re-align the main user display with the camera; (e) the processor executes software to calculate the vector created between the probe center and the target wireless tag center; (f) the processor executes software that aligns the virtual camera in the user display with the vector; and (g) the endoscope and the user display are displayed in the same orientation. This process can be repeated as necessary if the endoscope has moved to an extent that the alignment is no longer accurate.

With reference to FIG. 8 and FIG. 9, a device 200 including a wireless probe 204 and a handle 208 removably coupled to the wireless probe 204. In some embodiments, the wireless probe 204 includes a wireless tag similar to those described herein. For embodiments where the wireless probe 204 includes a single wireless tag, the wireless tag is as large as possible without impacting port compatibility (e.g., the ability for the wireless probe 204 to pass through a given diameter circle). In some embodiments, the wireless probe 204 includes at least two wireless tags. For embodiments where the wireless probe 204 includes two wireless tags, the two wireless tags are positioned with an angle formed therebetween. In some embodiments, the angle between the two wireless tags in the wireless probe is up to approximately 90 degrees.

The wireless probe 204 includes a first end 212 and a second end 216 opposite the first end 212. In the illustrated embodiment, the first end 212 is tapered and includes a point. The handle 208 is removably coupled to the second end 216 of the wireless probe 204. In some embodiments, the handle 208 engages the wireless probe 204 with a releasable interference fit. In other embodiments, the handle selectively engages the wireless probe with a latch, a release, a hook, or any other suitable mechanism.

The wireless probe 204 assists with localizing another wireless tag that has been implanted within a patient, for example. See, for example, FIG. 3. In other words, the device 200 is a wirelessly tracked tool where the wireless probe 204 is localized in response to electromagnetic fields (e.g., the electromagnetic fields generated by an exciter coil).

The device 200 is configured for manual operation and/or robotic operation. As one example of manual operation, the handle 208 can be attached to the wireless probe 204 and a user physically moves the wireless probe via the handle 208. As another example of manual operation, the wireless probe 204 is grasped by a surgical tool (e.g., a surgical forceps) operated by a user. In some embodiments, handle 208 is replaced with the use of the surgical tool. For robotic operation, the handle 208 can be removed from the wireless probe 204 and the wireless probe 204 is directly grasped by, for example, a robotic actuator or a robotically operated surgical tool. In some embodiments, the wireless probe 204 includes a durable soft exterior that is easily grasped by robotic actuators. In other words, the wireless probe 204 includes a soft material that covers an outer shell such that the wireless probe 204 is easily grasped by either hand operated or robotically operated graspers.

Figure 10:
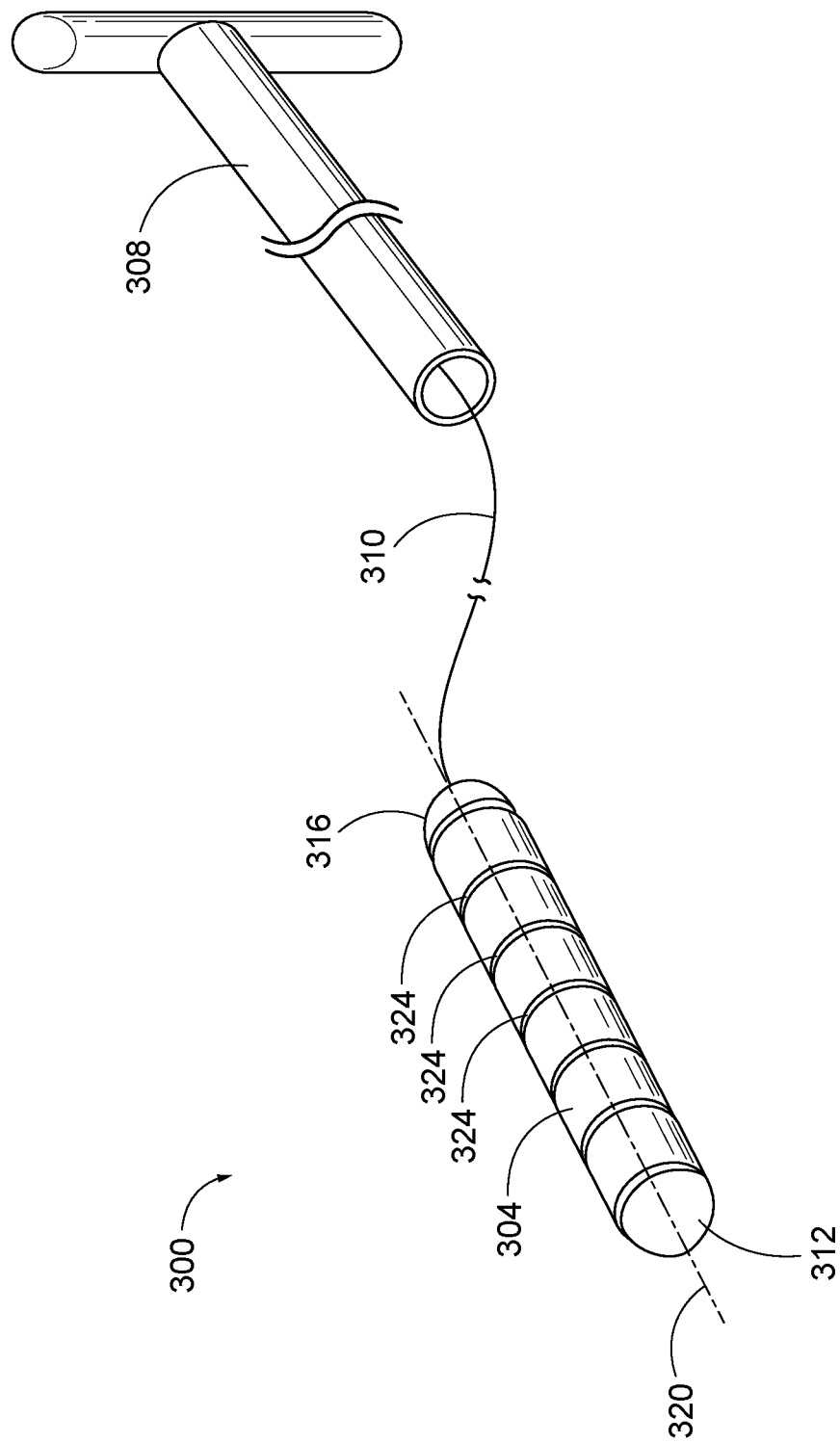
FIG. 10 is a perspective view of a device including a wireless probe, a detachable handle, and a tether.

With reference to FIG. 10, a device 300 includes a wireless probe 304, a handle 308 removably coupled to the wireless probe 304, and a flexible tether 310 coupled to the wireless probe 304. The wireless probe 304 includes a first end 312 and a second end 316 opposite the first end 312. The handle 308 is removably coupled to the second end 316 of the wireless probe 304. An axis 320 extends between the first end 312 and the second end 316. When the handle 308 is coupled to the second end 316 of the wireless probe 304, the handle 308 is aligned with the axis 320. In the illustrated embodiment, the wireless probe 304 includes a plurality of length markings 324 that are spaced along the axis 320. In some embodiments, the spacing between adjacent markings 324 is equal.

The flexible tether 310 is positioned within the handle 308 when the handle 308 is coupled to the second end 316 of the wireless probe 304. In other words, the flexible tether 310 is exposed if and/or when the handle 308 is removed from the wireless probe 304. In some embodiments, the handle is separable from the tether. In other embodiments, the handle is retained on the tether (e.g., a user slides the handle back and the tether remains within the handle core). The tether 310 can be utilized to receive the wireless probe if the wireless probe is dropped, for example, by a human or robot operator. In other words, the tether 310 allows for easy removal or retrieval of the wireless probe 304 from a cavity. In some embodiments, the tether is not included. In some embodiments, the handle is not included.

Figure 11:
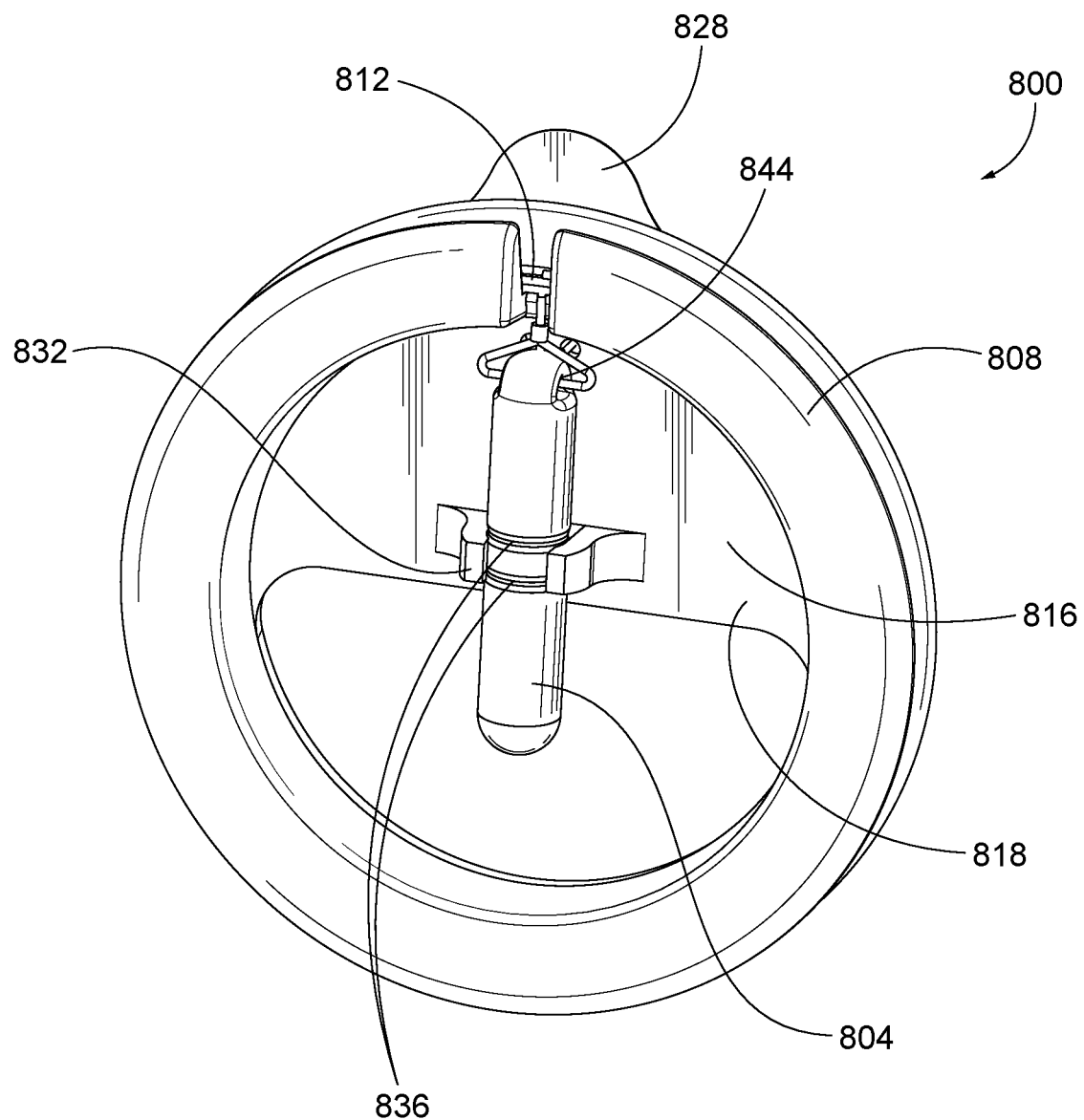
FIG. 11 is a front perspective view of a device including a wireless tag and a spool.
Figure 12:
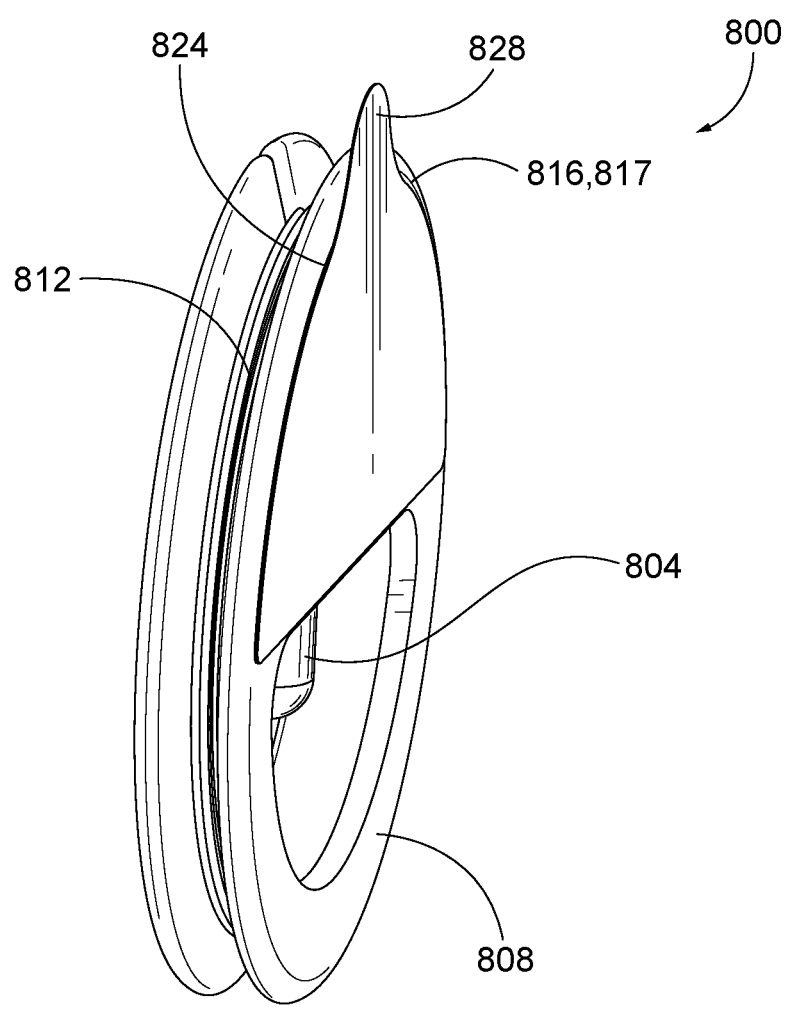
FIG. 12 is a rear perspective view of the device of FIG. 11
Figure 13:
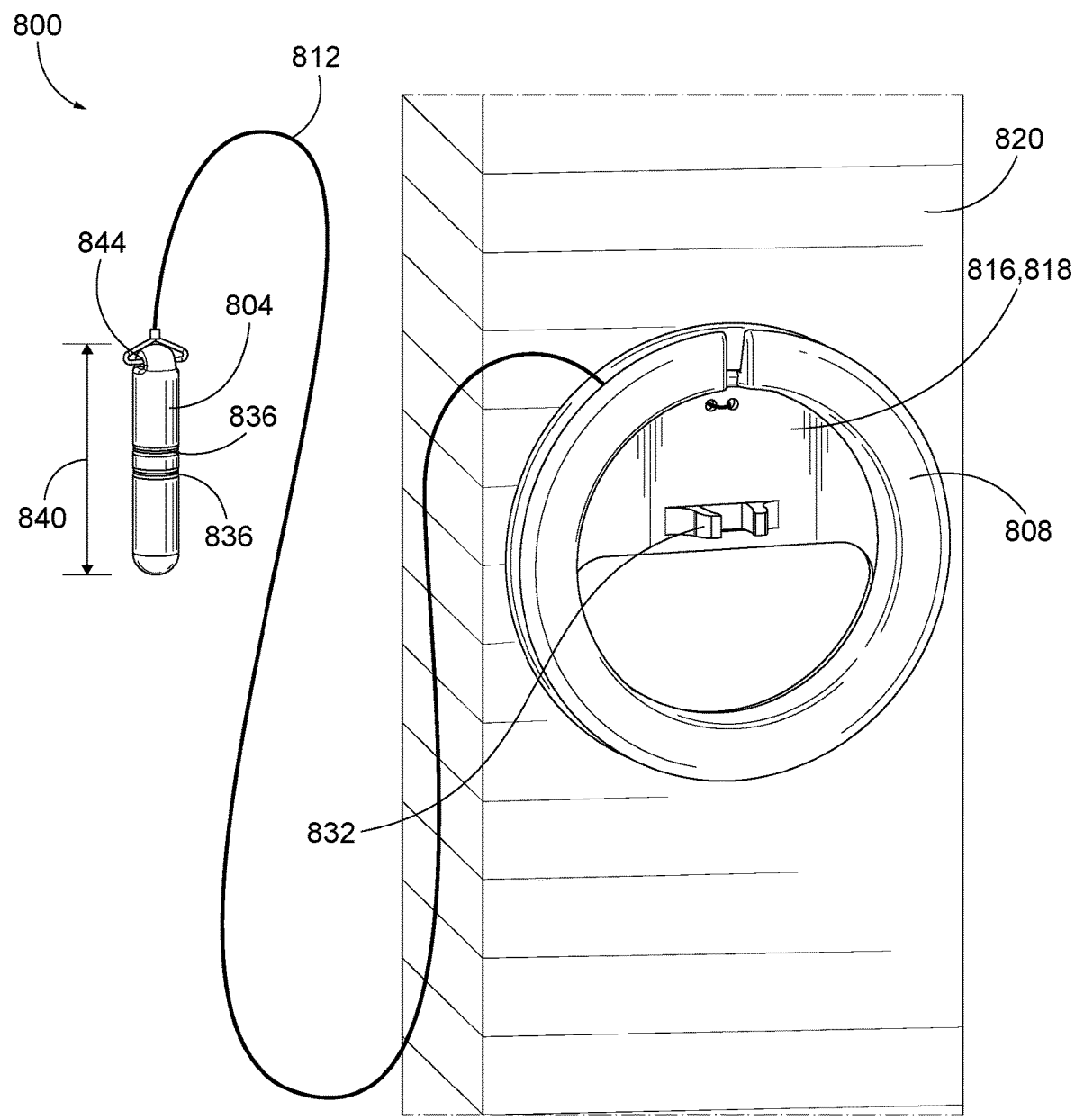
FIG. 13 is a perspective view of the device of FIG. 11 with the spool attached to working environment and the wireless tag spaced from the spool.

With reference to FIGS. 11-13, a device 800 includes a wireless tag 804, a spool 808, and a tether 812 extending between the wireless tag 804 and the spool 808. The spool 808 includes a mount portion 816 and the spool 808 is configured to be attached to a workspace 820 by the mount portion 816 (FIG. 13). In the illustrated embodiment, the mount portion 806 includes an adhesive 824 with a removable backing 828.

With reference to FIG. 11, the device 800 includes a clip 832 configured to at least partially receive the wireless tag 804. In other words, the wireless tag 804 is positioned within the clip 832 in a storage configuration. In the storage configuration, the tether 812 is wound around the spool 808. In the illustrated embodiment, the adhesive 824 is positioned on a first side 817 of the mount portion 816 and the clip 832 is positioned on a second side 818 of the mount portion 816.

With continued reference to FIGS. 11 and 13, the wireless tag 804 includes a plurality of markings 836 spaced along a length 840 of the wireless tag 804. In the illustrated embodiment, the markings 836 are equally spaced along the length 840 of the wireless tag 804. The wireless tag 804 further includes an aperture 844 formed at one end. The tether 812 extends through the aperture 844 and is secured to the wireless tag 804.

With reference to FIG. 13, in operation, the spool 808 is attached to the working environment 820 and the tether 812 is at least partially unwound from the spool 808 with the wireless tag 804 spaced from the spool 808. The wireless tag 804 of the device 800 can be deployed (e.g., positioned within a patient) and localized without any electrical wires connected to the wireless tag 804, but the tether 812 advantageously allows for the wireless tag 804 to be easily retrieved, for example, by a surgeon after a procedure is complete.

Figure 15:
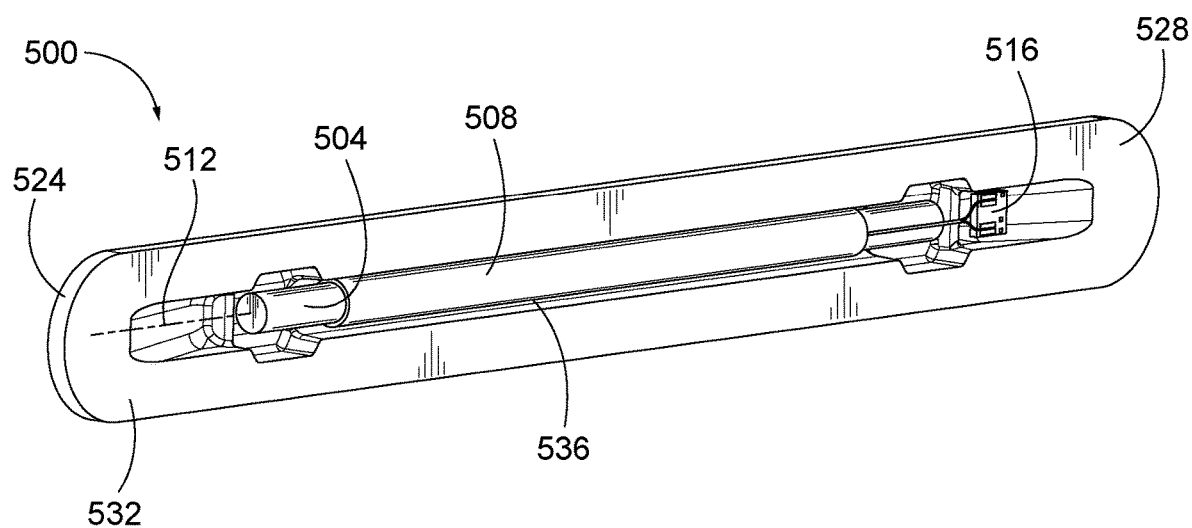
FIG. 15 is a rear perspective view of the wireless tag of FIG. 14.
Figure 16:
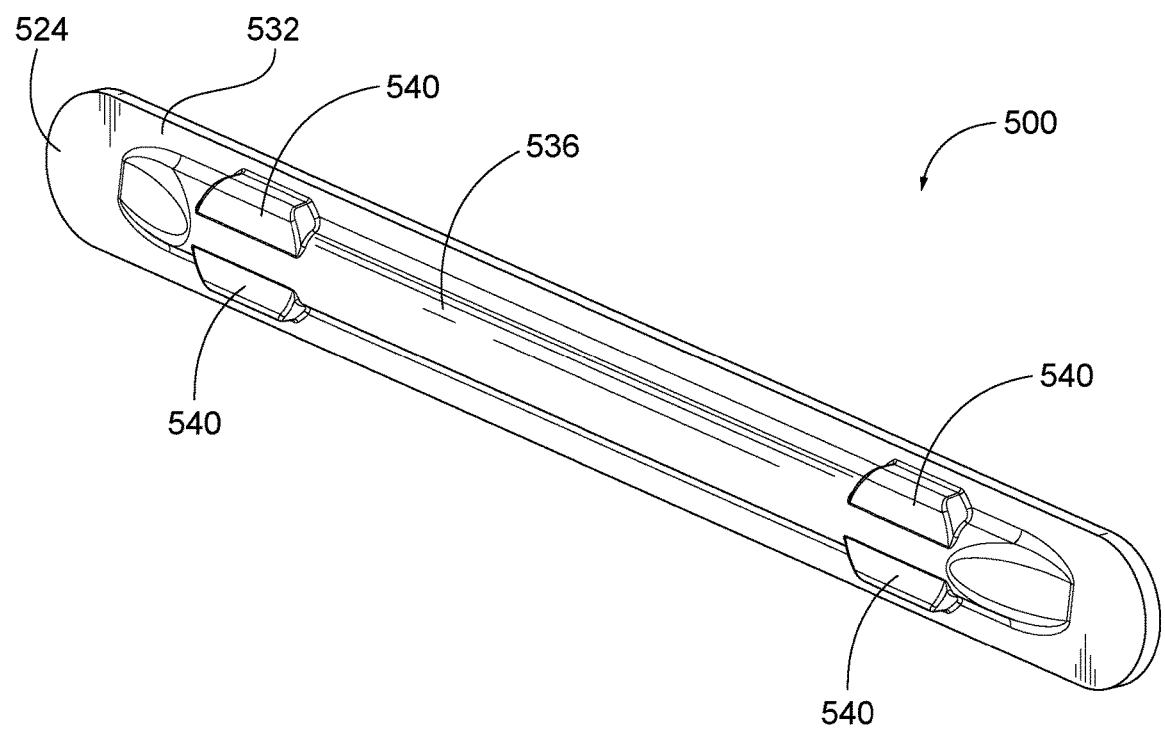
FIG. 16 is a front perspective view of the wireless tag of FIG. 15.

With reference to FIGS. 15 and 16, a wireless tag 500 is illustrated. In some embodiments, the wireless tag 500 corresponds to either one or both of the wireless tag 404 and the wireless tag 408. The wireless tag 500 includes a rod 504 and a coil 508 coupled to the rod 504. In some embodiments, the rod 504 is a ferrite rod. Ferrite is advantageous to have high permeability ($\mu'$) and low complex permeability ($\mu''$) at operating frequency. High permeability increases inductance and low complex permeability decreases core losses. In some embodiments, the rod 504 has a large aspect ratio (e.g., length to diameter ratio is large). In some embodiments, the length of the rod 504 is within a range of approximately 15 mm to approximately 20 mm. In some embodiments, the diameter of the rod 504 is within a range of approximately 0.6 mm to approximately 0.75 mm.

The coil 508 includes several turns wound around the rod 504. In some embodiments, the coil 508 includes a number of turns around the rod 504 within a range of approximately 500 to approximately 1000. In some embodiments, the number of turns is within a range of approximately 400 to approximately 1200. In some embodiments, the coil 508 is made of wire within a range of 47 AWG and 53 AWG. In some embodiments, the coil 508 has a number of layers of turns within a range of 1 layer to 3 layers. In some embodiments, the turns and layers of the coil 508 are selected to produce an inductance in a range of approximately 2 mH and approximately 5 mH. In the illustrated embodiment, the rod 504 and the coil 508 are aligned with an axis 512.

The wireless tag 500 further includes an integrated circuit chip 516 electrically coupled to the coil 508. In some embodiments, the integrated circuit chip 516 is a contactless identification device. In some embodiment, the wireless tag 500 further includes a high magnetic permeability backing. In some embodiments, the backing is Flux Field Directional Material (FFDM) EM25TP available from 3M™. In some embodiments, the backing has a relative permeability ($\mu'$) of approximately 2000. In some embodiment, the backing is positioned between the rod 504 and the tool, to increase overall inductance and Q valve.

The wireless tag 500 further includes a shell 524. In some embodiments, the rod 504, the coil 508, and the integrated circuit chip 516 are positioned within the shell 524. In some embodiments, the high magnetic permeability backing is positioned within the shell 524. The wireless tag 500 further includes an adhesive layer 528. In the illustrated embodiment, the adhesive layer 528 is coupled to the shell 524. In some embodiment, the adhesive layer 528 couples the wireless tag 500 to a tool surface (e.g., the side 422 of the jaw 412, FIG. 14). In other words, the wireless tag 500 is configured to be secured to a tool with the adhesive layer 528. In some embodiments, the wireless tag 500 is potted, glued, or epoxied to a tool surface.

With continued reference to FIG. 16, the shell 524 includes a flange 532, a recess 536 to receive the rod 504 and at least one protrusion 540. In the illustrated embodiment, the shell 524 includes a plurality of protrusions 540. As detailed further herein, the protrusions 540 advantageously ensures correct loading within, for example, an applicator (e.g., applicator 600, FIG. 17A). In some embodiments, the shell 524 is formed of glass.

With reference to FIG. 17A-17D, an applicator 600 for applying the wireless tags 404, 408 to the tool head 400 is illustrated. The applicator 600 includes a mount 616 with a groove 620 configured to receive at least a portion of the tool head 400. The applicator 600 includes a first slide 624 movable with respect to the mount 616 along an application axis 628 (FIG. 17C) and a second slide 632 movable with respect to the mount 616 along the application axis 628. Before the wireless tags 404, 408 are applied to the tool head 400, the first wireless tag 404 is coupled to and movable with the first slide 624, and the second wireless tag 408 is coupled to and movable with the second slide 632. In the illustrated embodiment, the wireless tags 404, 408 include an adhesive (e.g., the adhesive layer 528, FIG. 15) oriented toward the groove 620. In other words, adhesive on the wireless tags 404, 408 is oriented toward the tool head 400 when the tool is coupled to the mount 616.

Figure 17A:
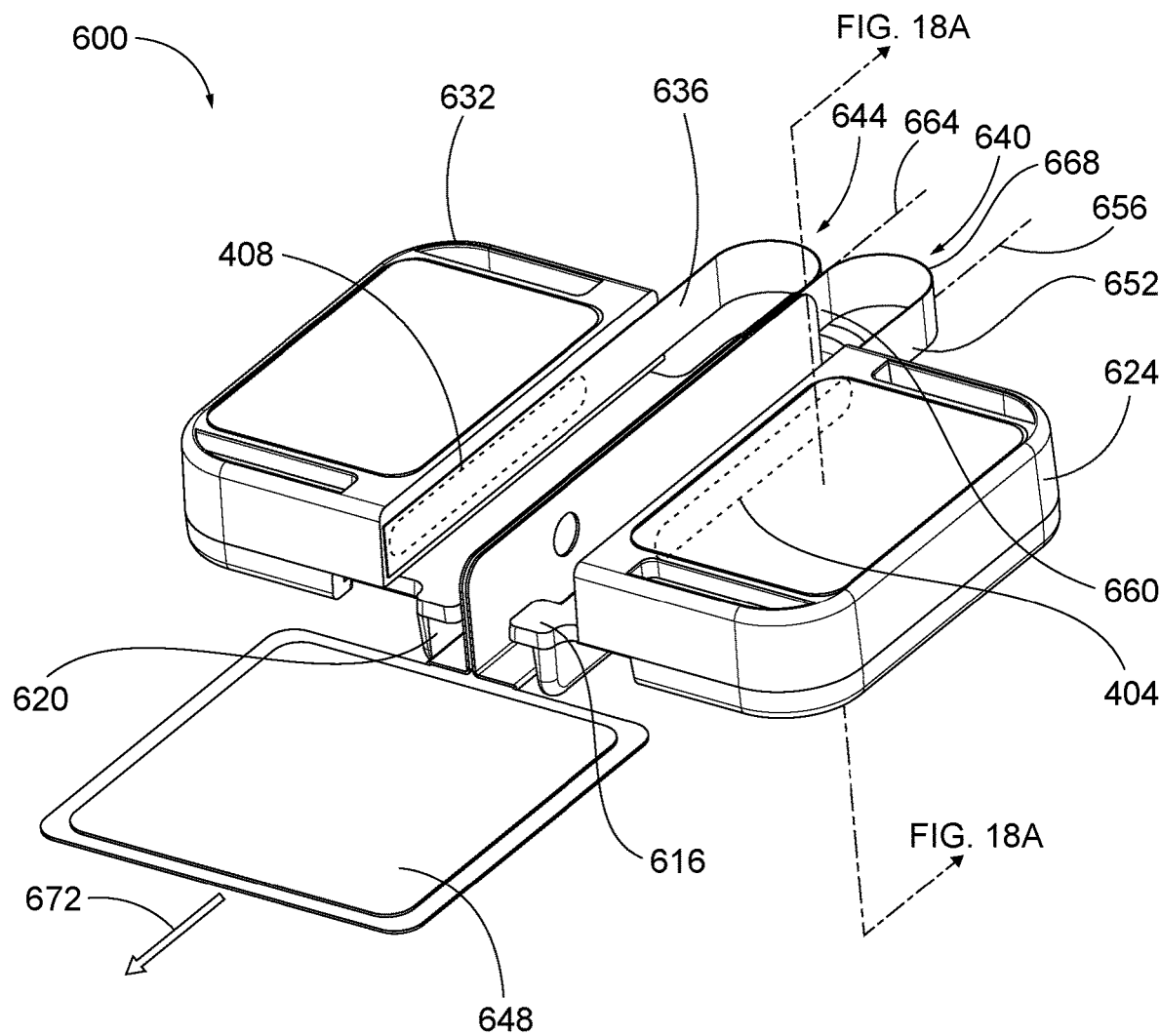
FIG. 17A is a perspective view of an applicator for applying wireless tags to a surgical stapler, shown in a storage configuration.

With reference to FIG. 17A, the applicator 600 includes a removable backing 636 coupled to the first slide 624 and the second slide 632. The removable backing 636 includes a first side 640 that abuts the adhesive of the first wireless tag 404 and a second side 644 that abuts the adhesive of the second wireless tag 408. The removable backing 636 includes a graspable portion 648 that is graspable by a user to pull and remove the removable backing 636 from the applicator 600—exposing the wireless tags 404, 408. Each side 640, 644 includes a first portion 652 extending along a first axis 656 from the graspable portion 648, a second portion 660 extending along a second axis 664, and an arcuate portion 668 positioned between the first portion 652 and the second portion 660. In the illustrated embodiment, the second axis 664 is spaced apart and parallel to the first axis 656. Advantageously, the entire removable backing 636 is removable from both the first wireless tag 404 and the second wireless tag 408 with a single pulling motion of the graspable portion 648 by a user. In other words, the adhesives on both wireless tags 404, 408 are exposed in response to a user pulling the graspable portion 648 in a removal direction 672.

Figure 17B:
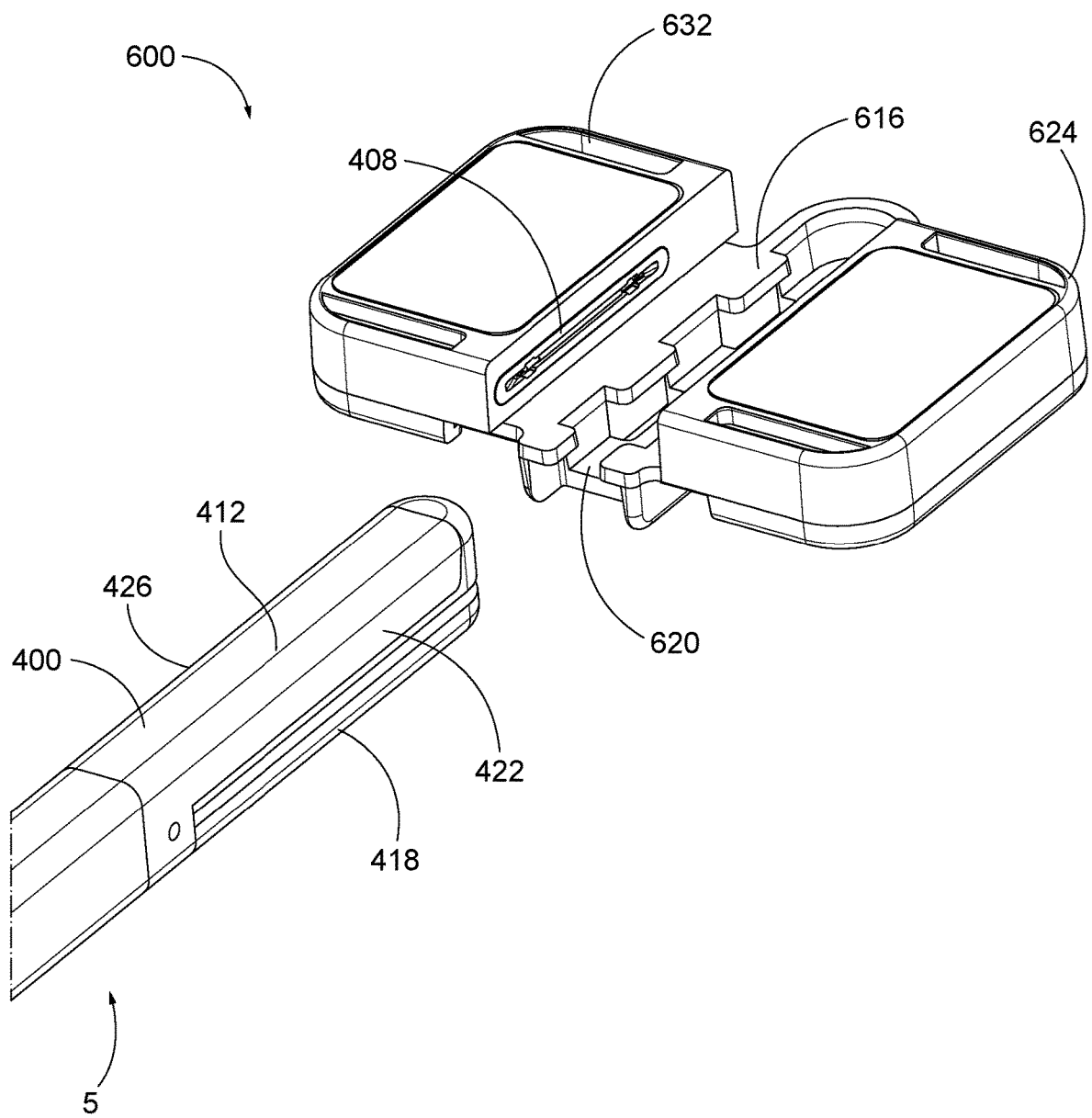
FIG. 17B is a perspective view of a surgical stapler and an applicator, with the applicator shown in a ready configuration.

With reference to FIG. 17B, in the illustrated embodiment, the tool is a surgical stapler and the groove 620 receives a portion of the second jaw 418 of the stapler head 400.

Figure 17C:
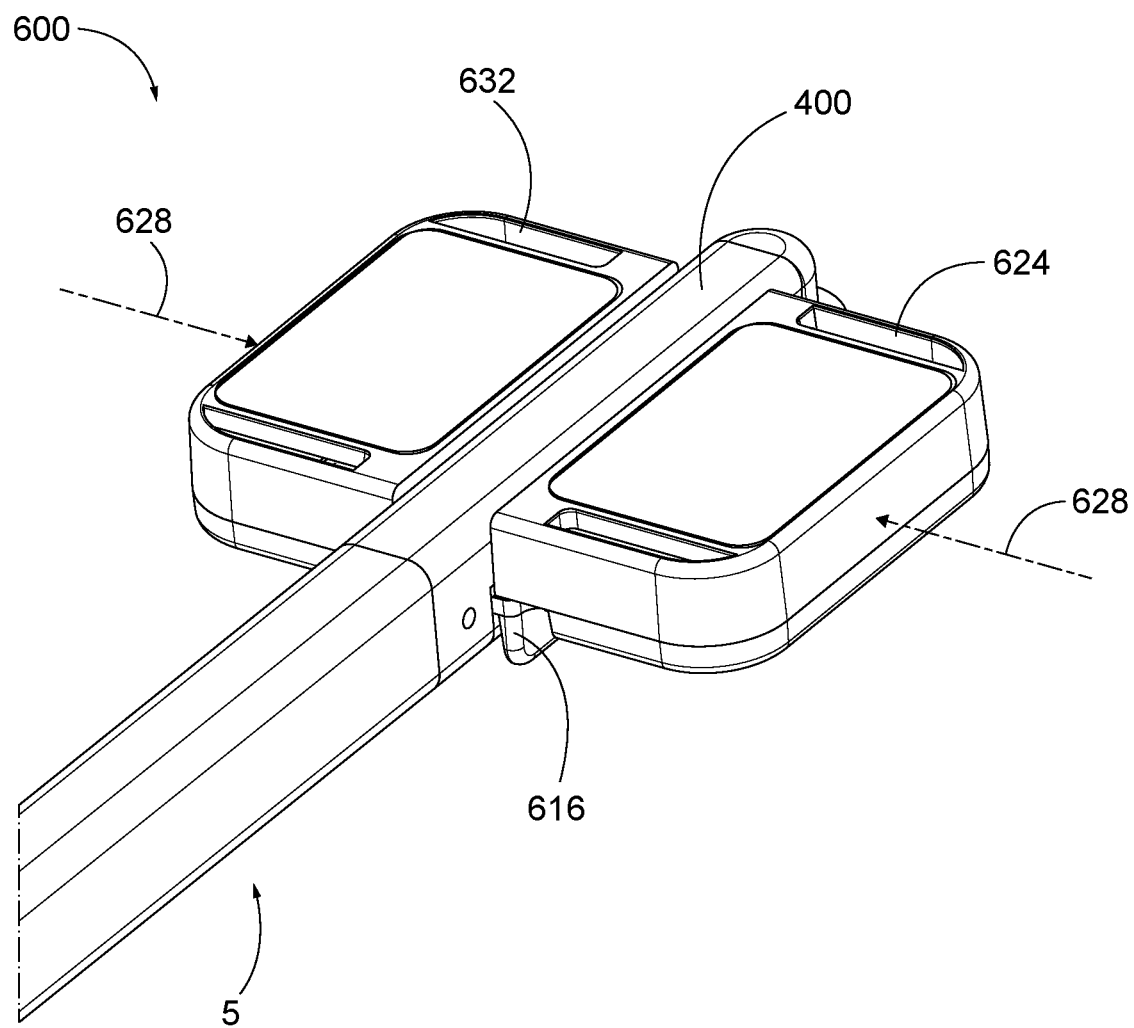
FIG. 17C is a perspective view of a surgical stapler mounted to an applicator, with the applicator shown in an actuated configuration.

With reference to FIG. 17C, the wireless tags 404, 408 are coupled to the tool head 400 in response to the slides 624, 632 moving along the application axis 628. Specifically, once the tool head 400 is in place on the applicator 600, a user moves the slides 624, 632 along the axis 628 to mount the wireless tags 404, 408 onto the tool 5.

Figure 17D:
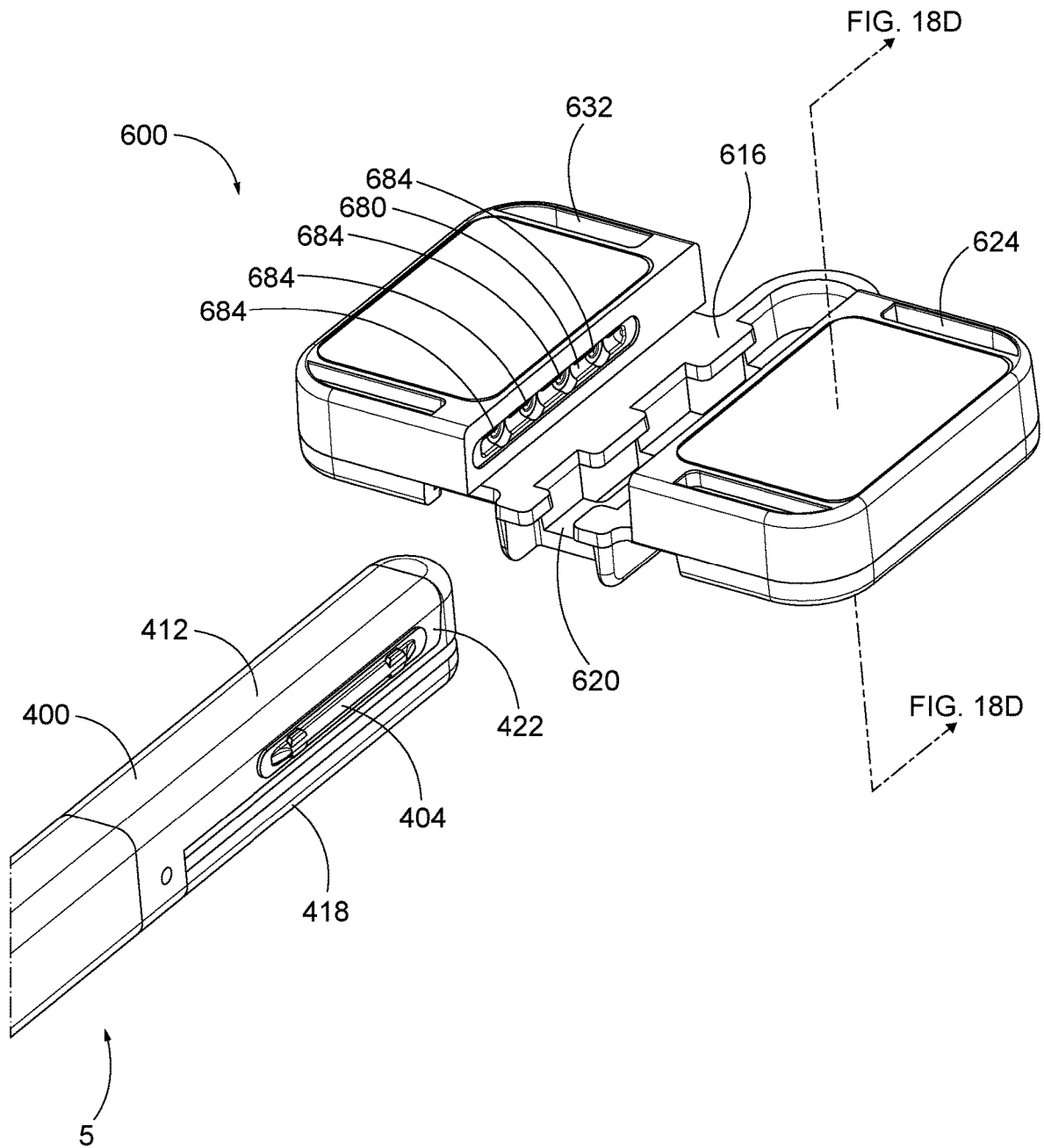
FIG. 17D is a perspective view of a surgical stapler removed from an applicator, with wireless tags mounted to the surgical stapler and the applicator shown in a used configuration.

With reference to FIG. 17D, after contacting the tool head 400, the slides 624, 632 are retracted away from the tool head 400, leaving the wireless tags 404, 408 coupled to the tool 5. In the illustrated embodiment, the wireless tag 404 is coupled to the side surface 422 of the jaw 412, and the wireless tag 408 is coupled to an opposite side surface 426 of the jaw 412. Advantageously, the applicator 600 physically aligns the stapler head 400 and jaws 412, 418 to ensure the wireless tags 404, 408 are applied at the correct positions on the stapler 5.

Figure 18A:
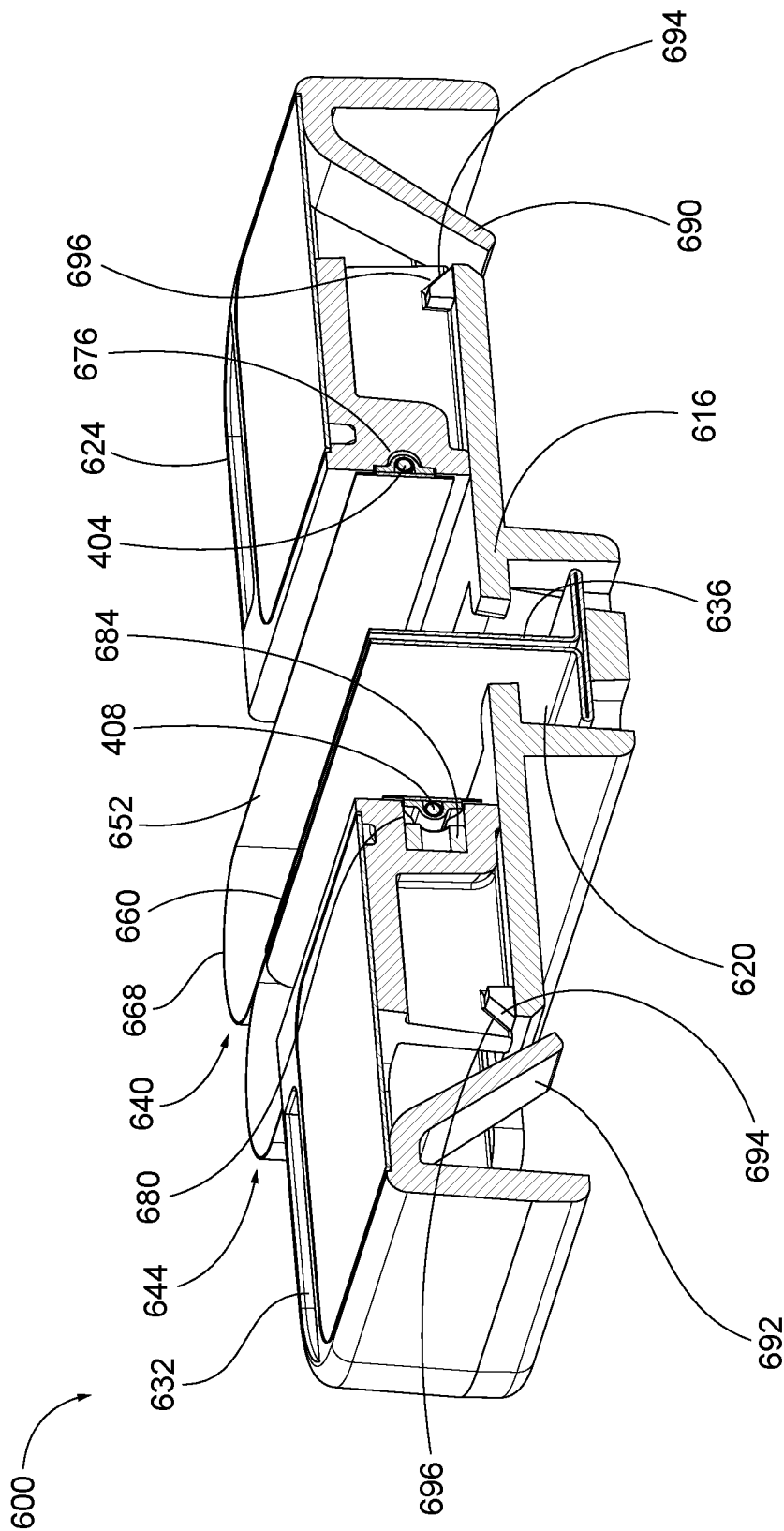
FIG. 18A is a perspective view of a cross-section of the applicator taken along lines 18A-18A, shown in FIG. 17A.
Figure 19:
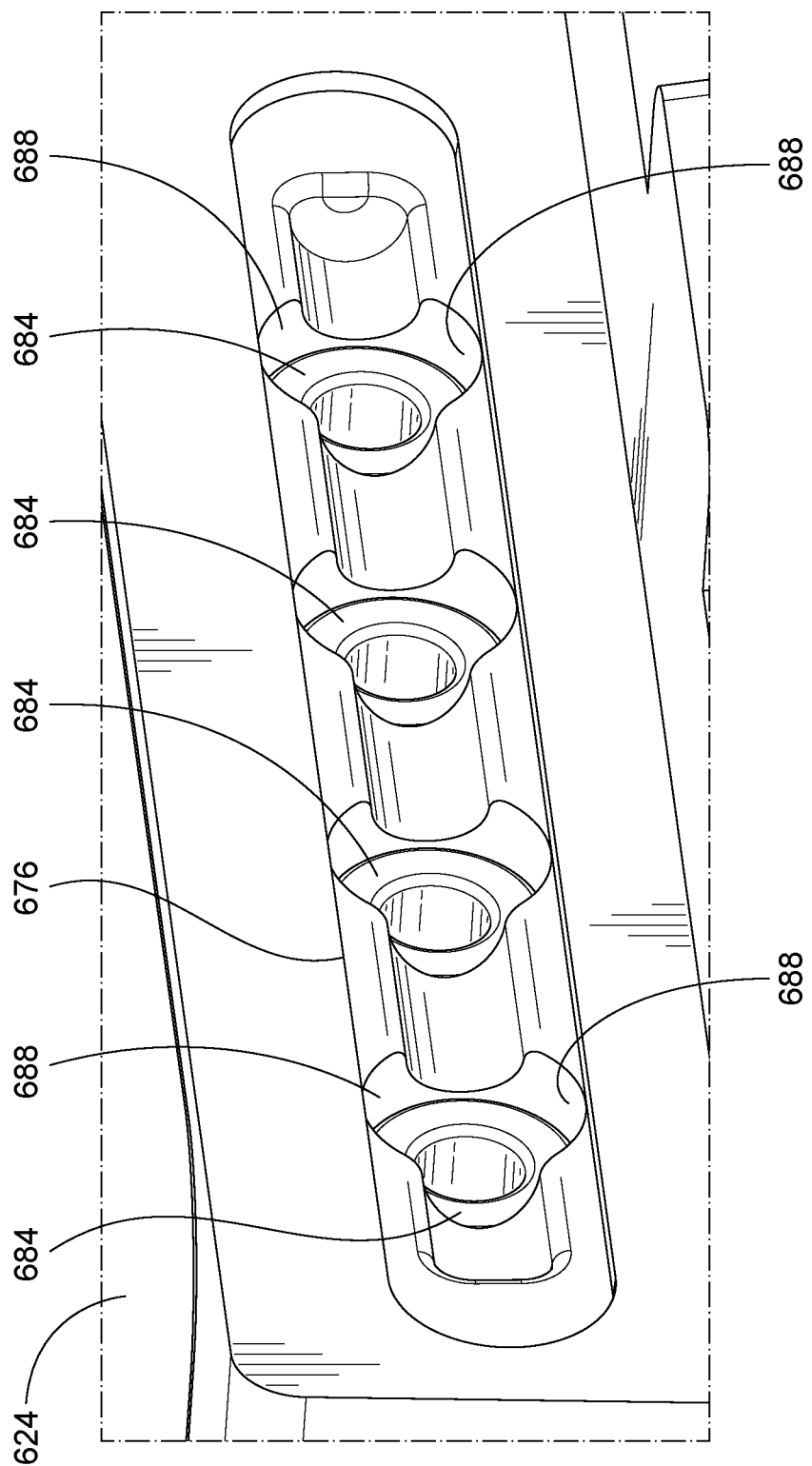
FIG. 19 is a perspective view of a portion of the applicator of FIG. 17D.
Figure 20:
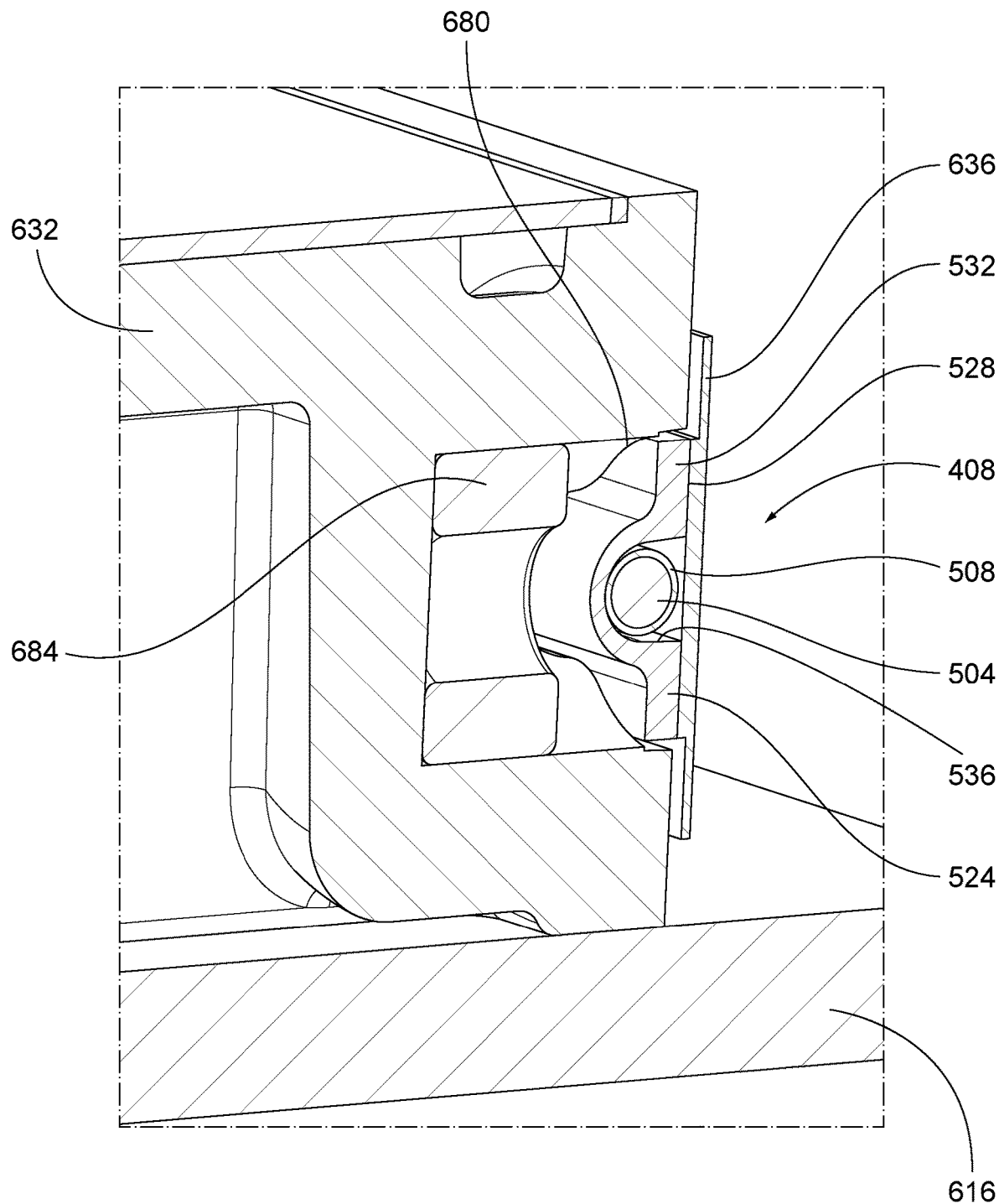
FIG. 20 is a perspective cross-sectional view of the applicator of FIG. 17A.

With reference to FIGS. 17D, 18A, 19 and 20, the first slide 624 includes a first cavity 676 that at least partially receives the first wireless tag 404. Similarly, the second slide 632 includes a second cavity 680 that at least partially receives the second wireless tag 408. At least one magnet 684 is positioned within the first cavity 676 and is magnetically coupled to the first wireless tag 404 (e.g., the ferromagnetic rod 504). With reference to FIG. 19, in the illustrated embodiment, a plurality of magnets 684 are positioned within the cavity 676 to magnetically support the wireless tag 404 within the cavity 676 before the wireless tag 404 is attached to the surgical stapler head 400.

With continued reference to FIG. 19, the cavity 676 includes notches 688. In some embodiments, the notches 688 facilitate insertion of the magnets 684. In some embodiments, the notches 688 receive the protrusions 540 formed on the shell 524 of the wireless tag 404. In other words, the cavity 676 includes the notch 688 and the first wireless tag 404 includes the shell 524 with the protrusion 540 position within the notch 688 when the applicator 600 is in the configurations shown in FIGS. 17A and 17B.

Figure 18B:
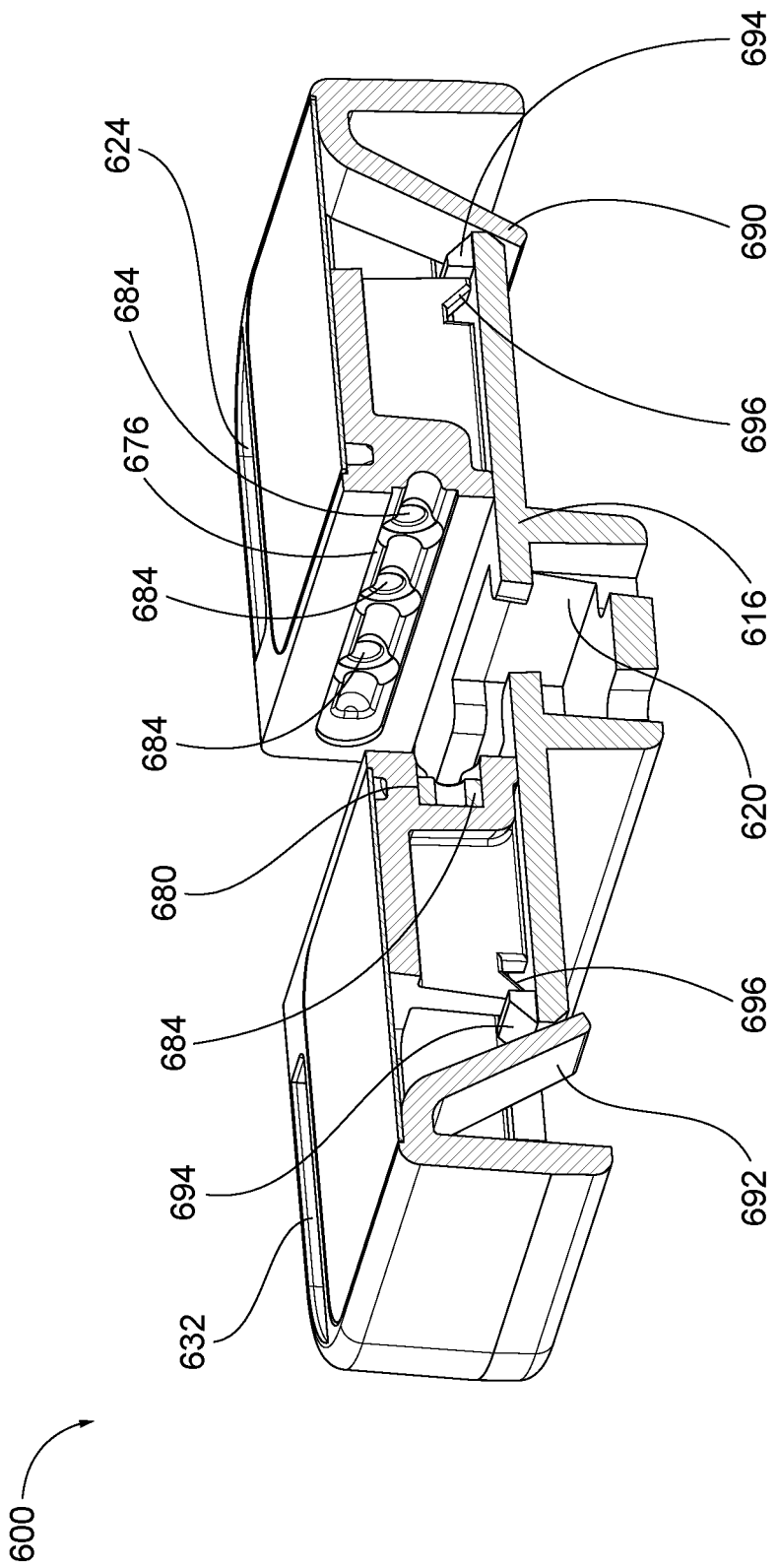
FIG. 18B is a perspective view of a cross-section of the applicator taken along lines 18B-18B, shown in FIG. 17D.

With reference to FIGS. 18A and 18B, the first slide 624 includes a spring lever 690 and the second slide 632 includes a spring lever 692. The spring lever 690 abuts a portion of the mount 616 as the first slide 624 moves relative to the mount 616. Likewise, the spring lever 692 abuts a portion of the mount 616 as the second slide 632 moves relative to the mount 616. In the illustrated embodiment, the spring lever 690, 692 deflect in response to the slides 624, 632, respectively, moving along the application axis 628 to attach the wireless tag 404, 408 to the stapler head 400. After the compression of the slides 624, 632 is removed, the spring levers 690, 692 biases the slides 624, 632 away from the groove 620 and the stapler head 400 positioned within the groove 620. In other words, as the slides 624, 632 are compressed by a user, the spring levers 690, 692 deflect as they abut the mount 616. When the slides 624, 632 are released by the user, the spring levers 690, 692 bias the slides 624, 632 away from the tool head 400. Advantageously, the slides 624, 632 are biased away from the head 400 after the wireless tags 404, 408 are attached to the tool head 400 with enough distance to provide clearance for the wireless tags 404, 408 to exit the applicator 600 without contacting the applicator 600 as the surgical tool 5 is removed from the applicator 600. In other words, the spring levers 690, 692 bias the slides 624, 632 outwards to provide clearance for the wireless tags 404, 408 as they are removed with the stapler head 400.

With continued reference to FIGS. 18A and 18B, the mount 616 further includes a ramp portion 694 and the first slide 624 includes a cam portion 696. Likewise, the second slide 632 includes cam portion 696 corresponding to another ramp portion 694 formed on the mount 616. The cam portion 696 is configured to slide relative to the ramp portion 694 in response to the slide 624, 632 moving along the application axis 628. In some embodiments, the wireless tag applicator 600 generates an audible feedback (e.g., a click) in response to the first slide 624 and/or the second slide 632 moving along the application axis 628. In the illustrated embodiment, an audible click is generated in response to the cam portions 696 clearing the ramp portions 694 on the mount 616. Advantageously, the audible feedback signals to a user the slides 624, 632 have been compressed a sufficient distance to successfully apply the wireless tags 404, 408 to the stapler head 400.

Various features and advantages are set forth in the following claims.

What is claimed is:

1. A wireless localization system comprising:
   an exciter coil;
   a sensor coil;
   a surgical stapler including a head defining a longitudinal axis; wherein the surgical stapler includes a first jaw and a second jaw;
   a first wireless tag positioned on a first side of the first jaw at a first position along the longitudinal axis; the first wireless tag configured to generate a first signal in response to a magnetic field generated by the exciter coil;
   a second wireless tag positioned on a second side of the first jaw at a second position along the longitudinal axis, the second position is spaced from the first position, the second wireless tag configured to generate a second signal in response to the magnetic field generated by the exciter coil; and a processor that determines a location of the head based on the first signal and the second signal detected by the sensor coil;
wherein the first wireless tag includes a first ferrite rod and a first coil wound around the first ferrite rod; and wherein the second wireless tag includes a second ferrite rod and a second coil would around the second ferrite rod; and wherein the first ferrite rod is oriented parallel to the second ferrite rod; and
wherein the first ferrite rod and the second ferrite rod are oriented parallel to the longitudinal axis of the head.

2. The system of claim 1, wherein the system further includes a third wireless tag configured to generate a third signal in response to the magnetic field generated by the exciter coil; and wherein the processor determines the location of the head with respect to the third wireless tag based on the first signal, the second signal, and the third signal detected by the sensor coil.

3. The system of claim 1, wherein the processor determines an orientation of the head.

4. The system of claim 1, wherein the first wireless tag defines a first volume no greater than 60 mm³, and the second wireless tag defines a second volume no greater than 60 mm³.

5. The system of claim 1, wherein the first wireless tag further includes an integrated circuit chip in electrical communication with the first coil.

6. The system of claim 5, wherein the first wireless tag includes a shell, and wherein the first ferrite rod, the first coil, and the integrated circuit chip are positioned within the shell.

7. The system of claim 6, further including a magnetic permeability backing positioned within the shell.

8. The system of claim 5, wherein the first wireless tag has a thickness within a range of 0.3 mm to 0.8 mm.

9. The system of claim 1, wherein the first wireless tag includes an adhesive layer, and the first wireless tag is secured to the head with the adhesive layer.

10. The system of claim 1, wherein the first wireless tag further includes a secondary coil, wherein the first coil is spaced from the secondary coil along the longitudinal axis.

11. The system of claim 1, wherein the magnetic field generated by the exciter coil is within a range of 1 µT to 50 µT at a frequency within a range of 125 kHz to 150 kHz.

12. The system of claim 11, wherein the first wireless tag has an inductance value at the frequency within a range of 0.5 mH to 20 mH.

13. The system of claim 11, wherein the first wireless tag has a quality factor within a range of 5 to 20, wherein the quality factor is defined as the ratio of inductive reactance to resistance at the frequency.

14. The system of claim 1, further comprising a user display including a perspective view of a virtual head shown at the location of the head.

15. The system of claim 14, wherein the user display includes a top-down view, a side view, an endoscopic camera view, or any combination thereof.

16. The system of claim 14, wherein the user display includes a partial spherical shell that indicates a relative position of the head with respect to a third wireless tag.

17. The system of claim 16, wherein the user display includes a shortest distance path extending between the virtual head and the partial spherical shell.

18. The system of claim 17, wherein the virtual head includes a marker to indicate the location the shortest distance path intersects the virtual head.

19. The system of claim 1, wherein the first wireless tag is positioned a first distance to a distal tip of the head and the second wireless tag is positioned a second distance to the distal tip; wherein the first distance is shorter than the second distance.

20. The system of claim 1, wherein the head is configured to pass through a 12 mm port.

* * * * *